US007666404B2

(12) United States Patent
Ulrich et al.

(10) Patent No.: US 7,666,404 B2
(45) Date of Patent: Feb. 23, 2010

(54) GLANDERS/MELIODOSIS VACCINES

(75) Inventors: Ricky Ulrich, Hagerstown, MD (US); Jeffrey Jeddeloh, Oakville, MO (US); Petra Oyston, Salisbury (GB)

(73) Assignee: The United States of America as represented by the Secretary of the Army, Washington, DC (US)

( * ) Notice: Subject to any disclaimer, the term of this patent is extended or adjusted under 35 U.S.C. 154(b) by 260 days.

(21) Appl. No.: 10/620,242

(22) Filed: Jul. 15, 2003

(65) Prior Publication Data

US 2004/0171020 A1 Sep. 2, 2004

Related U.S. Application Data

(60) Provisional application No. 60/396,257, filed on Jul. 15, 2002.

(51) Int. Cl.
*A61K 48/00* (2006.01)
*A01N 63/00* (2006.01)

(52) U.S. Cl. .................................... 424/93.2; 424/93.4

(58) Field of Classification Search ................. 424/93.1
See application file for complete search history.

(56) References Cited

U.S. PATENT DOCUMENTS 6,413,751 B1 7/2002 Benkovic et al.

OTHER PUBLICATIONS

DeShazer et al (Microbial Pathogenesis vol. 30, pp. 253-269, May 2001).*

Callahan and Dunlap, 2000. LuxR- and acyl-homoserin-lactone-controlled non-*lux* genes define a quorum-sensing regulon in *Vibrio fischeri*. J. of Bacteriology 182, 2811-2822.

Nasser, W. et al., 1998. Characterization of the *Erwinia chrysanthemi expl-expR* locus directing the synthesis of two N-acyl-homoserine lacton signal molecules. Molecular Microbiology 29, 1391-1405.

* cited by examiner

*Primary Examiner*—Mark Navarro
(74) *Attorney, Agent, or Firm*—Elizabeth Arwine

(57) ABSTRACT

The present invention relates to nucleic acids encoding *B. mallei* and *B. pseudomallei* AHL synthases and LuxR transcriptional regulators, and methods for use, as well as describes the construction, characterization and use of avirulent strains of *B. mallei* and methods of use.

7 Claims, 5 Drawing Sheets

```
                        SEQUENCE LISTING

<160> NUMBER OF SEQ ID NOS: 44

<210> SEQ ID NO 1
<211> LENGTH: 612
<212> TYPE: DNA
<213> ORGANISM: B. mallei ATCC 23344 AHS gene bmaI1

<400> SEQUENCE: 1

atgcgaactt tcgttcatgg cgacgggcgc ctgccgagcg                      40

acttggcggc tgatctgggc ctttatcggc acggagtttt                      80

cgtcgagcag ctcggctgga aactgccgtc ggcaagcgaa                     120

gggttcgagc gggatcagta cgatcgcgac gataccgtct                     160

atgtgttcgc ccgcgacgac gacggggaaa tctgcggctg                     200

cgcccggctg ctgccgacga cccgcccgta tctgctgaag                     240

gaactgttcc cgacgctggt cgcgcaagac atgccgttgc                     280

cgcaatccgc cgccgtctgg gaattgtcgc gcttcgccgc                     320

gaacgccgag gatccggccg ggggcggcaa cccggcctgg                     360
```

-continued

```
gcggtgcgcc cgatgctcgc cgccgtcgtc gagtgcgccg                    400

cgcggcttgg cgcgaagcaa ctgatcggcg tgacgtttct                    440

gagcatggag cgcctgttcc gccggatcgg cgtgcacgcg                    480

caccgggcgg ggcccgcgca gcagatcgac gggcgcatgg                    520

tcgtcgcgtg ctggatcgac ctcgacgcgc aaacgctcgc                    560

cgcgctcgat ctcgacccgc tgctgtgcgc gccgcccgcc                    600

gaagccgcct ga                                                  612
```

<210> SEQ ID NO 2
<211> LENGTH: 609
<212> TYPE: DNA
<213> ORGANISM: B. mallei ATCC 23344 AHS gene bmaI3

<400> SEQUENCE: 2

```
atgtcataca tcatcgcggg ccgattgaac gaactgccgc                     40

cgcacgtcca gaccgatctc ggcgcgtatc gctacgacgt                     80

gttcgtgcgc cggctcggct ggacgatcgc cggccactcg                    120

ctcgacgaac atgcggagtg ggacgagttc gacgggccgt                    160

cgacgattca tgtcgtcgcg ctcgacgacg cgcgcgagat                    200

ctgcggctac gcacgcctgc tgccgacgac gggcccgtat                    240

ctgctgcgcg acgtgtttgc gcatctgctc ggctcgtcgc                    280

ccgcgccgca atcgcctgcc gtctgggaaa tgtcgcgctt                    320

cgccgcgtcg cggcggcggc gaagcgcgac cgagcgcgag                    360

ccgctcggca tggcgttctt tccgtcggtg ctcacggtgg                    400

ccgcgtcgct cggcgcgacg cgcgtggtcg gcgtgatgac                    440

gccatcgatc gaacgcctgt accgccgctc gggcatcgcg                    480

ctgcatcgcc tcggcaacgc gatgccgggc gcgggcggca                    520

gcctgtccgc atgctcgatc gatctgccgc gcctcgcgtt                    560

cgcgccgttg ggcctcaagc agtgcgcggc gtgcctggcg                    600

atgcattga                                                      609
```

<210> SEQ ID NO 3
<211> LENGTH: 720
<212> TYPE: DNA
<213> ORGANISM: B. mallei ATCC 23344 transcriptional regulator gene bmaR1

<400> SEQUENCE: 3

```
atggaactgc gctggcaaga cgcctatctt caatttagcg                     40

ccgcggagaa cgagcagcag ctcttccaac agatcgccgc                     80

gtatacgaag cggctcggct tcgaatattg ctgctatggc                    120

atacgcgtgc cgttgccgat ctcgaagccg gtcgtcgcga                    160

ttttcgacac ctatccgaac ggctggatgg agcgctacca                    200

ggaaatgaac tacctggagg tcgatccgac cgtacgcgag                    240

ggcgcgctca gctcgaacat gatcgtctgg ccggaggcga                    280

gcgcgagcga cgcgacgacg ctctggagcg acgcgcgcga                    320
```

-continued

```
tcacgggctg gcggtcggcg tcgcgcagtc gagctgggcc                     360

tcgcgcgggg tgttcggtct cctgacgatc gcgcggcaca                     400

cggaccgcct gacgtccgcc gagatcaacc atctgacgtt                     440

gcaggcgaac tggctcgcga acatgtcgca ctcgctgatg                     480

agccgttttc tcgtgccgaa gctcgcgccc gaatcgggcg                     520

tggcgctcac gcaccgcgag cgggaggtgc tgtgctggac                     560

gggagagggc aagaccgcgt gcgagatcgg gcagatcctc                     600

agcatctccg agcgcacggt gaactttcac gtcaacaaca                     640

tcctcgacaa gctcggcgcg acgaacaagg tgcaggccgt                     680

cgtgaaggcg atcgcgatgg ggctcatcga cgcgccgtaa                     720
```

<210> SEQ ID NO 4
<211> LENGTH: 609
<212> TYPE: DNA
<213> ORGANISM: B. mallei ATCC 23344 transcriptional regulator gene bmaR3

<400> SEQUENCE: 4

```
atgtcataca tcatcgcggg ccgattgaac gaactgccgc                      40

cgcacgtcca gaccgatctc ggcgcgtatc gctacgacgt                      80

gttcgtgcgc cggctcggct ggacgatcgc cggccactcg                     120

ctcgacgaac atgcggagtg ggacgagttc gacgggccgt                     160

cgacgattca tgtcgtcgcg ctcgacgacg cgcgcgagat                     200

ctgcggctac gcacgcctgc tgccgacgac gggcccgtat                     240

ctgctgcgcg acgtgtttgc gcatctgctc ggctcgtcgc                     280

ccgcgccgca atcgcctgcc gtctgggaaa tgtcgcgctt                     320

cgccgcgtcg cggcggcggc gaagcgcgac cgaccgcgag                     360

ccgctcggca tggcgttctt tccgtcggtg ctcacggtgg                     400

ccgcgtcgct cggcgcgacg cgcgtggtcg gcgtgatgac                     440

gccatcgatc gaacgcctgt accgccgctc gggcatcgcg                     480

ctgcatcgcc tcggcaacgc gatgccgggc gcgggcggca                     520

gcctgtccgc atgctcgatc gatctgccgc gcctcgcgtt                     560

cgcgccgttg ggcctcaagc agtgcgcggc gtgcctggcg                     600

atgcattga                                                       609
```

<210> SEQ ID NO 5
<211> LENGTH: 660
<212> TYPE: DNA
<213> ORGANISM: B. mallei ATCC 23344 transcriptional regulator gene bmaR4

<400> SEQUENCE: 5

```
atgccgttgc cgatccgctg tggcgaaggg ccgtcgccgc                      40

agcagcgcgg tgcgccgcgt gcggcccgtc gcccgtcgag                      80

aacgctacgt tcggcgacga gaccgggggc gccgcgtgcg                     120

cggacggtct tgcgggcatg tcctgttcga tcgtcggccg                     160

acgcttgcgt cgtgcgtgtc gagtccgccg acaatcaccc                     200
```

-continued

```
gcagcggtct tcagcggtct ttcggcgcgc gacgcctggc                           240

ccgccatgcg tacgagggcg catggcgcag catgttcgcg                           280

gcctgccggg gcggcgtcga gcgtgcgcgg cggcagccgt                           320

gatgcaggtg tggccggcgc gcgcgggatt cgagcgatgc                           360

tcgagcgccg agcgccggtt cggcttcggc gcaggcggcc                           400

gattgtcccg ccgcgttcga cgaaacgaac ggcgtgccgt                           440

gcttcggcgg cgcggcaggc aagctcgccg gcgtttcgcc                           480

gcgcgcgggc cgccgttgcc ctctcgcccc tttcgagcac                           520

gctttcttca ttggttcgct aacgtaactt cctcacttga                           560

gctgggcggt tctatgttcg aaggcttgtc cattggttcg                           600

tttaacgaaa ttctgaacgc gacttgcaag aagagcctct                           640

ttgagcagac ggcgtatcac                                                 660
```

<210> SEQ ID NO 6
<211> LENGTH: 726
<212> TYPE: DNA
<213> ORGANISM: B. mallei ATCC 23344 transcriptional regulator gene bmaR5

<400> SEQUENCE: 6

```
atgagggcgg cgatggggaa ctgggcggag gatctgctgg                            40

cggggctcga cagcgcacga tccgaggaag aggcgtttcg                            80

aagcgtcgaa accgcggcgg cggcgctcga tttcgaatac                           120

tgcgcatacg ggctgcgcgt gccgtggccg ctgtccaggc                           160

cgcgcatcga gacgcgcagc aactttcccg agcaatggaa                           200

gcggcgctac gtcgaggcgg gtttcctcga tgtcgatccg                           240

attctcgcgc acggccgccg atcgcagcaa ccggtcgtcc                           280

tcgccgagac gctgtttgcg tccgcgcacc agatgtgggt                           320

cgaggcgcag tcgttcgggt tgcggttcgg ctgggcgcag                           360

tcgagcttcg acgcgtatgg cggcatgggc atgctcgcgc                           400

tcgtccgctc gcgcgagccg gtgacggcgg cggaactcga                           440

cgcgaaggag taccggatgc gctggctcgt gcgcaccgcg                           480

cacgccgcgc tcggccgcat gatgttgccc aagctgatgg                           520

cggacccgga gcgcgggctg accgagcgcg aggtcgaggt                           560

gctcaagtgg gcggcggacg gcaagacgtc cggcgagatc                           600

tcgaagatcc tcgcgatatc cgtcgatacg gtgaatttcc                           640

acgtgaagaa cgcgatcctg aagctcagga cggcgaacaa                           680

gacggcggcc gtcgtgcgcg cggcgatgct cgggttgctg                           720

agctga                                                                726
```

<210> SEQ ID NO 7
<211> LENGTH: 612
<212> TYPE: DNA
<213> ORGANISM: B. pseudomallei DD503 AHS gene bpmI1

<400> SEQUENCE: 7

-continued

```
atgcgaactt tcgttcatgg cgacgggcgc ctgccgagcg        40

acttggcggc tgatctgggc ctttatcggc acggagtttt        80

cgtcgagcag ctcggctgga aactgccgtc ggcaagcgaa       120

gggttcgagc gggatcagta cgatcgcgac gataccgtct       160

atgtgttcgc ccgcgacgac gacggggaaa tctgcggctg       200

cgcccggctg ctgccgacga cccgcccgta tctgctgaag       240

gaactgttcc cgacgctggt cgcgcaagac atgccgttgc       280

cgcaatccgc cgccgtctgg gaattgtcgc gcttcgccgc       320

gaacgccgag gatccggccg gggcggcaa cccggcctgg        360

gcggtgcggc cgatgctcgc cgccgtcgtc gagtgcgccg       400

cgcggcttgg cgcgaagcaa ctgatcggcg tgacgtttct       440

gagcatggag cgcctgttcc gccggatcgg cgtgcacgcg       480

caccgggcgg ggcccgcgca gcagatcgac gggcgcatgg       520

tcgtcgcgtg ctggatcgac ctcgacgcgc aaacgctcgc       560

cgcgctcgat ctcgacccgc tgctgtgcgc gccgcccgcc       600

gaagccgcct ga                                     612
```

<210> SEQ ID NO 8
<211> LENGTH: 621
<212> TYPE: DNA
<213> ORGANISM: B. pseudomallei DD503 AHS gene bpmI2

<400> SEQUENCE: 8

```
atgatcgata cgaccgtcat aagcgccgcg caactggatt        40

ccaccgtcaa ggcagcactc ggcaattatc gtcgggcgat        80

attcatcgag aaactcggct ggccattgcc gttggtcgac       120

gggctcgaga tcgatcagtt cgatcgtccc gatacgattt       160

acgtggtcgg caaaacagag tccggcgata tctgcggatg       200

cgcccgcctg ctgcccacga cgaggcccta cctgctcgga       240

gaggtgttcc ccgatctgat gggcgacgcg gcgccgccct       280

gctcggcgca cgtgtgggaa atctcgcgat tttcgtcttc       320

gatcctctcc ggagggccgg acgcgctgcg gcaggctcac       360

cgcaatacgc gcatcctgct cgcgaaaatc gtccgctttg       400

cgcaggcggc cggcgtgaag cggctgatca ccgtttcgcc       440

gctcgcagtc gagcggctgc tcaaccgtct gaaagtccat       480

attcaccgcg cgggtccgcc tcggttgatc gacggcaagc       520

cggtgttcgc gtgctggatc gaggtggacg acatcacgct       560

ccaagcgctc gacatcgagc cggccgccga ttcggccgcc       600

ggcgcgctgc gccattcgtg a                           621
```

<210> SEQ ID NO 9
<211> LENGTH: 609
<212> TYPE: DNA
<213> ORGANISM: B. pseudomallei DD503 AHS gene bpmI3

-continued

<400> SEQUENCE: 9

```
atgtcataca tcatcgcggg ccgattgaac gaactgccgc     40
cgcacgtcca gaccgatctc ggcgcgtatc gctacgacgt     80
gttcgtgcgc cggctcggct ggacgatcgc cggccactcg    120
ctcgacgaac atgcggagtg ggacgagttc gacgggccgt    160
cgacgattca tgtcgtcgcg ctcgacgacg cgcgcgagat    200
ctgcggctac gcacgcctgc tgccgacgac gggcccgtat    240
ctgctgcgcg acgtgtttgc gcatctgctc ggctcgtcgc    280
ccgcgccgca atcgcctgcc gtctgggaaa tgtcgcgctt    320
cgccgcgtcg cggcggcggc gaagcgcgac cgagcgcgag    360
ccgctcggca tggcgttctt tccgtcggtg ctcacggtgg    400
ccgcgtcgct cggcgcgacg cgcgtggtcg gcgtgatgac    440
gccatcgatc gaacgcctgt accgccgctc gggcatcgcg    480
ctgcatcgcc tcggcaacgc gatgccgggc gcgggcggca    520
gcctgtccgc atgctcgatc gatctgccgc gcctcgcgtt    560
cgcgccgttg ggccgcaagc agtgcgcggc gtgcctggcg    600
atgcattga                                      609
```

<210> SEQ ID NO 10
<211> LENGTH: 720
<212> TYPE: DNA
<213> ORGANISM: B. pseudomallei DD503 transcription regulator gene bpmR1

<400> SEQUENCE: 10

```
atggaactgc gctggcaaga cgcctatctt caatttagcg     40
ccgcggagaa cgagcagcag ctcttccaac agatcgccgc     80
gtatacgaag cggctcggct tcgaatattg ctgctatggc    120
atacgcgtgc cgttgccgat ctcgaagccg gtcgtcgcga    160
ttttcgacac ctatccgaac ggctggatgg agcgctacca    200
ggaaatgaac tacctggagg tcgatccgac cgtacgcgag    240
ggcgcgctca gctcgaacat gatcgtctgg ccggaggcga    280
gcgcgagcga cgcgacgacg ctctggagcg acgcgcgcga    320
tcacgggctg gcggtcggcg tcgcgcagtc gagctgggcc    360
tcgcgcgggg tgttcggtct cctgacgatc gcgcggcaca    400
ccgaccgcct gacgtccgcc gagatcaacc atctgacgtt    440
gcaggcgaac tggctcgcga acatgtcgca ctcgctgatg    480
agccgttttc tcgtgccgaa gctcgcgccc gaatcgggcg    520
tggcgctcac gcaccgcgag cgggaggtgc tgtgctggac    560
gggggagggc aagaccgcgt gcgagatcgg gcagatcctc    600
agcatctccg agcgcacggt gaactttcac gtcaacaaca    640
tcctcgacaa gctcggcgcg acgaacaagg tgcaggccgt    680
cgtgaaggcg atcgcgatgg ggctcatcga cgcgccgtaa    720
```

-continued

<210> SEQ ID NO 11
<211> LENGTH: 711
<212> TYPE: DNA
<213> ORGANISM: B. pseudomallei DD503 transcription regulator gene bpmR2

<400> SEQUENCE: 11

```
atggagatgc acgactttct tcaattttgg ctaaacgaat      40
tttcacgcag tgagaaccca cagcacgtca tttccgtctt      80
gacccgcgcg gccgcgacgc tcggctacga atacgccgcc     120
tacggcatgc gccgcccctt tccgatcagc aatccgccga     160
tcctcatggt gtccaactat cccgcccgat ggcaggaacg     200
ctatatcgaa gcgcgattcg cgaacatcga cggcgcggtg     240
aaggccgcgc tcggcagcga ccggcccgtg acctggagcg     280
cgcccgccaa cgcatcgaaa agcgcattct gggcggaggc     320
gctgtcgttc ggcatcgccc acggctggtc gtccgcgtcg     360
cggggcgcgg acggcgcgat cggcgtgctg acgctgtcga     400
gaacgcagga cccgatcgac accgcggaga agtttcgcaa     440
cgagagcatc gtgcactggc tcgccaatgt cgctcatgcg     480
tcgatggcgc cgttcctgcc cgccgccgac gagttcgatc     520
cggacctcac gcgccgcgag accgatgtgc tgaaatggac     560
ggccgacgga aagacagcgt acgaaatcgc gctgattctc     600
agcatctcgg agagcaccgt caattttcac gtgaagaata     640
tcgtctccaa gctgggctcc acgaacaaga tacaggccgt     680
ggccaaggcc gcgctgatgg ggatgctgtg a              711
```

<210> SEQ ID NO 12
<211> LENGTH: 693
<212> TYPE: DNA
<213> ORGANISM: B. pseudomallei DD503 transcription regulator gene bpmR3

<400> SEQUENCE: 12

```
atgctctccg ccgcgttgcc ggaatcgcgc gacgtccgca      40
cgctggtcga gactttcagg caggcggcgc tgcagatcgg      80
ctaccagcac catgcgatcg tcgagctgtc gggcgcatcg     120
catccggcgt cgatcgacgt cgtctcgctg cactatccgt     160
ccgagtgggt cgagcactac acccgcaacg actacttcgc     200
gatcgatccc gtccatcgcg cggcattccg ctacagcacg     240
ccgttctcgt ggaacgacgt cgcgacggcg aacctgcgcg     280
agcggcatct gctgatggaa gccgaggacg cgggcctcga     320
caacggcatc agcatcccgc tgcatcagcc gctcggacgc     360
gtgctgctgg tgagcctgtc cggcaccgcg ccgacgcacg     400
atgccgatgc gaaatggcgc aacgcgtacc tgctcggcat     440
gcagttcaat ctgcagttcc agagcatgcg cacgtgccgc     480
ccgattccgc cgtccgtcca cctgacggat cgcgaacaga     520
tgtgcctcac gtgggtcgcg cgcggcaagt cgtcgtgggt     560
```

-continued

```
catcgcgaac atgctcgaca tctccaaata cacggtcgac    600

ttccacatcg agaacgcgat ggagaagctc aacacgcgca    640

gccgcacgtt cgccgccgtg aaggcgacgc ggcaggggct    680

catctttcca tga                                 693
```

<210> SEQ ID NO 13
<211> LENGTH: 885
<212> TYPE: DNA
<213> ORGANISM: B. pseudomallei DD503 transcription regulator gene bpmR4

<400> SEQUENCE: 13

```
atggcgcgaa cgcgccgagg ggcaagcgaa tcgcgccgca     40

gcgcgcgcgc cggcgcgata gccgcgcgac ctgcgttccg     80

cgcccgccgc acaggcgggt cgccgcgcgg tcgcgcgcaa    120

ccgcttgcgc gcggcggcgg cgcgcgctca gatcaacccg    160

cgcgccgatg cgatgacgac cgcctgcgcg cggttgttcg    200

cgcctatctt gcgtgcggcg ttcgacagat gaaacacgac    240

cgtgcgctcc gagatgccga gaatcttcga gatttcccac    280

gccgtcttgc cgcgccccgc ccactgcagc gattcgcgct    320

cgcgcgcggt cagatcgcac gagccctgcc gtctgagccg    360

gcaatcgagc agctcgtgca tcgccgcgtg cacgaagctc    400

gcgagcaact gcgacaggct cagcagccgc agtatgtcgc    440

tcgcgtcgtg ctcgaacgga tcgtcggtcg ccatgctgag    480

catgctgatc gcgccgctgc gatcgtgaac ggggcaactg    520

agcccgtaga cgaggccgta cgatttcgcc tcgtcgcgca    560

tgagcttcgc gcggctggtc gtatagaggt cgtcgtgcca    600

gatgagcggc acggtccggc accggcaatg ctgaacgacg    640

ggatcgatcg acaggtagtc ggcggcgtcg tagcgcagcc    680

gccactcggc cggaaatccg tcgagcatgc agcggctcga    720

cgccgcgccg gagatctgat gccggtacgc gaaattcttg    760

aagcccagtt ggcgaacgtg atacgccgtc tgctcaaaga    800

ggctcttctt gcaagtcgcg ttcagaattt cgttaaacga    840

accaatggac aagccttcga acatagaacc gcccagctca    880

agtga                                          885
```

<210> SEQ ID NO 14
<211> LENGTH: 726
<212> TYPE: DNA
<213> ORGANISM: B. pseudomallei DD503 transcription regulator gene bpmR5

<400> SEQUENCE: 14

```
atgagggcgg cgatggggaa ctgggcggag gatctgctgg     40

cggggctcga cagcgcacga tccgaggaag aggcgtttcg     80

aagcgtcgaa accgcggcgg cggcgctcga tttcgaatac    120

tgcgcatacg ggctgcgcgt gccgtggccg ctgtccaggc    160

cgcgcatcga gacgcgcagc aactttcccg agcaatggaa    200
```

-continued

```
gcggcgctac gtcgaggcgg gtttcctcga cgtcgatccg    240

attctcgcgc acggccgccg atcgcagcaa ccggtcgtcc    280

tcgccgagac gctgtttgcg tccgcgcacc agatgtgggt    320

cgaggcgcag tcgttcggtt tgcggttcgg ctgggcgcag    360

tcgagcttcg acgcgtatgg cggcatgggc atgctcgcgc    400

tcgtccgctc gtgcgagccg gtgacggcgg cggaactcga    440

cgcgaaggag taccggatgc gctggctcgt gcgcaccgcg    480

cacgccgcgc tcggccgcat gatgttgccc aagctgatgg    520

cggacccgga gcgcgggctg accgagcgcg aggtcgaggt    560

gctcaagtgg gcggcggacg gcaagacgtc cggcgagatc    600

tcgaagatcc tcgcgatatc cgtcgatacg gtgaatttcc    640

acgtgaagaa cgcgatcctg aagctcagga cggcgaacaa    680

gacggcggcc gtcgtgcgcg cggcgatgct cgggttgctg    720

agctga                                         726
```

```
<210> SEQ ID NO 15
<211> LENGTH: 203
<212> TYPE: PRT
<213> ORGANISM: B. mallei ATCC 23344 bmaI1

<400> SEQUENCE: 15

Met Arg Thr Phe Val His Gly Asp Gly Arg
 1              5                   10

Leu Pro Ser Asp Leu Ala Ala Ala Leu Gly
                15                  20

Leu Tyr Arg His Gly Val Phe Val Glu Gln
                25                  30

Leu Gly Trp Lys Leu Pro Ser Ala Ser Glu
                35                  40

Gly Phe Glu Arg Asp Gln Tyr Asp Arg Asp
                45                  50

Asp Thr Val Tyr Val Phe Ala Arg Asp Asp
                55                  60

Gly Glu Ile Cys Gly Cys Ala Arg Leu Leu
                65                  70

Pro Thr Thr Arg Pro Tyr Leu Leu Lys Glu
                75                  80

Lys Phe Pro Thr Leu Val Ala Gln Asp Met
                85                  90

Pro Leu Pro Gln Ser Ala Ala Val Trp Glu
                95                  100

Leu Ser Arg Phe Ala Ala Asn Ala Glu Asp
                105                 110

Pro Ala Gly Gly Gly Asn Pro Ala Trp Ala
                115                 120

Val Arg Pro Met Leu Ala Ala Val Val Glu
                125                 130

Cys Ala Ala Arg Leu Gly Ala Lys Gln Leu
                135                 140
```

-continued

```
Ile Gly Val Thr Phe Leu Ser Met Glu Arg
                145                 150

Leu Phe Arg Arg Ile Gly Val His Ala His
                155                 160

Arg Ala Gly Pro Ala Gln Gln Ile Asp Gly
                165                 170

Arg Met Val Val Ala Cys Trp Ile Asp Leu
                175                 180

Asp Ala Gln Thr Leu Ala Ala Leu Asp Leu
                185                 190

Asp Leu Pro Leu Leu Cys Ala Pro Pro Ala
                195                 200

Glu Ala Ala


<210> SEQ ID NO 16
<211> LENGTH: 202
<212> TYPE: PRT
<213> ORGANISM: B. mallei ATCC 23344 bmaI3

<400> SEQUENCE: 16

Met Ser Tyr Ile Ile Ala Gly Arg Leu Asn
 1               5                  10

Glu Lys Pro Pro His Val Gln Thr Asp Leu
                15                  20

Gly Ala Tyr Arg Tyr Asp Val Phe Val Arg
                25                  30

Arg Leu Gly Trp Thr Ile Ala Gly His Ser
                35                  40

Leu Asp Glu His Ala Glu Trp Asp Glu Phe
                45                  50

Asp Gly Pro Ser Thr Ile His Val Val Ala
                55                  60

Leu Asp Asp Ala Arg Glu Ile Cys Gly Tyr
                65                  70

Ala Arg Leu Leu Pro Thr Thr Gly Pro Tyr
                75                  80

Leu Leu Arg Asp Val Phe Ala His Leu Leu
                85                  90

Gly Ser Ser Pro Ala Pro Gln Ser Pro Ala
                95                  100

Val Trp Glu Met Ser Arg Phe Ala Ala Ser
                105                 110

Arg Arg Arg Arg Ser Ala Thr Glu Arg Glu
                115                 120

Pro Leu Gly Met Ala Phe Phe Pro Ser Val
                125                 130

Leu Thr Val Ala Ala Ser Leu Gly Ala Thr
                135                 140

Arg Val Val Gly Val Met Thr Pro Ser Ile
                145                 150

Glu Arg Leu Tyr Arg Arg Ser Gly Ile Ala
                155                 160

Leu His Arg Leu Gly Asn Ala Met Pro Gly
                165                 170
```

-continued

```
Ala Gly Gly Ser Leu Ser Ala Cys Ser Ile
                175                 180

Asp Leu Pro Arg Leu Ala Phe Ala Pro Leu
                185                 190

Gly Leu Lys Gln Cys Ala Ala Cys Leu Ala
                195                 200

Met His


<210> SEQ ID NO 17
<211> LENGTH: 239
<212> TYPE: PRT
<213> ORGANISM: B. mallei ATCC 23344 bmaR1

<400> SEQUENCE: 17

Met Glu Leu Arg Trp Gln Asp Ala Tyr Leu
 1               5                  10

Gln Phe Ser Ala Ala Glu Asn Glu Gln Gln
                15                  20

Leu Phe Gln Gln Ile Ala Ala Tyr Thr Lys
                25                  30

Arg Leu Gly Phe Glu Tyr Cys Cys Tyr Gly
                35                  40

Ile Arg Val Pro Leu Pro Ile Ser Lys Pro
                45                  50

Val Val Ala Ile Phe Asp Thr Tyr Pro Asn
                55                  60

Gly Trp Met Glu Arg Tyr Gln Glu Met Asn
                65                  70

Tyr Leu Glu Val Asp Pro Thr Val Arg Glu
                75                  80

Gly Ala Leu Ser Ser Asn Met Ile Val Trp
                85                  90

Pro Glu Ala Ser Ala Ser Asp Ala Thr Thr
                95                  100

Leu Trp Ser Asp Ala Arg Asp His Gly Leu
                105                 110

Ala Val Gly Val Ala Gln Ser Ser Trp Ala
                115                 120

Ser Arg Gly Val Phe Gly Leu Leu Thr Ile
                125                 130

Ala Arg His Thr Asp Arg Leu Thr Ser Ala
                135                 140

Glu Ile Asn His Leu Thr Leu Gln Ala Asn
                145                 150

Trp Leu Ala Asn Met Ser His Ser Leu Met
                155                 160

Ser Arg Phe Leu Val Pro Lys Leu Ala Pro
                165                 170

Glu Ser Gly Val Ala Leu Thr His Arg Glu
                175                 180

Arg Glu Val Leu Cys Trp Thr Gly Glu Gly
                185                 190

Lys Thr Ala Cys Glu Ile Gly Gln Ile Leu
                195                 200
```

-continued

Ser Ile Ser Glu Arg Thr Val Asn Phe His
205 210

Val Asn Asn Ile Leu Asp Lys Leu Gly Ala
215 220

Thr Asn Lys Val Gln Ala Val Val Lys Ala
225 230

Ile Ala Met Gly Leu Ile Asp Ala Pro
235

<210> SEQ ID NO 18
<211> LENGTH: 202
<212> TYPE: PRT
<213> ORGANISM: B. mallei ATCC 23344 bmaR3

<400> SEQUENCE: 18

Met Ser Tyr Ile Ile Ala Gly Arg Leu Asn
1 5 10

Glu Leu Pro Pro His Val Gln Thr Asp Leu
15 20

Gly Ala Tyr Arg Tyr Asp Val Phe Val Arg
25 30

Arg Leu Gly Trp Thr Ile Ala Gly His Ser
35 40

Leu Asp Glu His Ala Glu Trp Asp Glu Phe
45 50

Asp Gly Pro Ser Thr Ile His Val Val Ala
55 60

Leu Asp Asp Ala Arg Glu Ile Cys Gly Tyr
65 70

Ala Arg Leu Leu Pro Thr Thr Gly Pro Tyr
75 80

Leu Leu Arg Asp Val Phe Ala His Leu Leu
85 90

Gly Ser Ser Pro Ala Pro Gln Ser Pro Ala
95 100

Val Trp Glu Met Ser Arg Phe Ala Ala Ser
105 110

Arg Arg Arg Arg Ser Ala Thr Glu Arg Glu
115 120

Pro Leu Gly Met Ala Phe Phe Pro Ser Val
125 130

Leu Thr Val Ala Ala Ser Leu Gly Ala Thr
135 140

Arg Val Val Gly Val Met Thr Pro Ser Ile
145 150

Glu Arg Leu Tyr Arg Arg Ser Gly Ile Ala
155 160

Leu His Arg Leu Gly Asn Ala Met Pro Gly
165 170

Ala Gly Gly Ser Leu Ser Ala Cys Ser Ile
175 180

Asp Leu Pro Arg Leu Ala Phe Ala Pro Leu
185 190

Gly Leu Lys Gln Cys Ala Ala Cys Leu Ala
195 200

-continued

Met His

<210> SEQ ID NO 19
<211> LENGTH: 220
<212> TYPE: PRT
<213> ORGANISM: B. mallei ATCC 23344 bmaR4

<400> SEQUENCE: 19

```
Met Pro Leu Pro Ile Arg Cys Gly Glu Gly
 1               5                  10

Pro Ser Pro Gln Gln Arg Gly Ala Pro Arg
                15                  20

Ala Ala Arg Arg Pro Ser Arg Thr Leu Arg
                25                  30

Ser Ala Thr Arg Pro Gly Ala Pro Arg Ala
                35                  40

Arg Thr Val Leu Arg Ala Cys Pro Val Arg
                45                  50

Ser Ser Ala Asp Ala Cys Val Val Arg Val
                55                  60

Glu Ser Ala Asp Asn His Pro Gln Arg Ser
                65                  70

Ser Ala Val Phe Arg Arg Ala Thr Pro Gly
                75                  80

Pro Pro Cys Val Arg Gly Arg Met Ala Gln
                85                  90

His Val Arg Gly Leu Pro Gly Arg Arg Arg
                95                  100

Ala Cys Ala Ala Ala Ala Val Met Gln Val
                105                 110

Trp Pro Ala Arg Ala Gly Phe Glu Arg Cys
                115                 120

Ser Ser Ala Glu Arg Arg Phe Gly Phe Gly
                125                 130

Ala Gly Gly Arg Leu Ser Arg Arg Val Arg
                135                 140

Arg Asn Glu Arg Arg Ala Val Leu Arg Arg
                145                 150

Arg Gly Arg Gln Ala Arg Arg Arg Phe Ala
                155                 160

Ala Arg Gly Pro Pro Leu Pro Ser Arg Pro
                165                 170

Phe Arg Ala Arg Phe Leu His Trp Phe Ala
                175                 180

Asn Val Thr Ser Ser Leu Glu Leu Gly Gly
                185                 190

Ser Met Phe Glu Gly Leu Ser Ile Gly Ser
                195                 200

Phe Asn Glu Ile Leu Asn Ala Thr Cys Lys
                205                 210

Lys Ser Leu Phe Glu Gln Thr Ala Tyr His
                215                 220
```

<210> SEQ ID NO 20

-continued

<211> LENGTH: 241
<212> TYPE: PRT
<213> ORGANISM: B. mallei ATCC 23344 bmaR5

<400> SEQUENCE: 20

Met Arg Ala Ala Met Gly Asn Trp Ala Glu
1 5 10

Asp Leu Leu Ala Gly Leu Asp Ser Ala Arg
15 20

Ser Glu Glu Glu Arg Phe Arg Ser Val Glu
25 30

Thr Ala Ala Ala Ala Leu Asp Phe Glu Tyr
35 40

Cys Ala Tyr Gly Leu Arg Val Pro Trp Pro
45 50

Leu Ser Arg Pro Arg Ile Glu Thr Arg Ser
55 60

Asn Phe Pro Glu Gln Trp Lys Arg Arg Tyr
65 70

Val Glu Ala Gly Phe Leu Asp Val Asp Pro
75 80

Ile Leu Ala His Gly Arg Arg Ser Gln Gln
85 90

Pro Val Val Leu Ala Glu Thr Leu Phe Ala
95 100

Ser Ala His Gln Met Trp Val Glu Ala Gln
105 110

Ser Phe Gly Leu Arg Phe Gly Trp Ala Gln
115 120

Ser Ser Phe Asp Ala Tyr Gly Gly Met Gly
125 130

Met Leu Ala Leu Val Arg Ser Arg Glu Pro
135 140

Val Thr Ala Ala Glu Leu Asp Ala Lys Glu
145 150

Tyr Arg Met Arg Trp Leu Val Arg Thr Ala
155 160

His Ala Ala Leu Gly Arg Met Met Leu Pro
165 170

Lys Leu Met Ala Asp Pro Glu Arg Glu Leu
175 180

Thr Glu Arg Glu Val Glu Val Leu Lys Trp
185 190

Ala Ala Asp Gly Lys Thr Ser Gly Glu Ile
195 200

Ser Lys Ile Leu Ala Ile Ser Val Asp Thr
205 210

Val Asn Phe His Val Lys Asn Ala Ile Leu
215 220

Lys Leu Arg Thr Ala Asn Lys Thr Ala Ala
225 230

Val Val Arg Ala Ala Met Leu Gly Leu Leu
235 240

Ser

-continued

<210> SEQ ID NO 21
<211> LENGTH: 203
<212> TYPE: PRT
<213> ORGANISM: B. pseudomallei DD503 bpmI1

<400> SEQUENCE: 21

```
Met Arg Thr Phe Val His Gly Asp Gly Arg
 1               5                  10

Leu Pro Ser Asp Leu Ala Ala Asp Leu Gly
                15                  20

Leu Tyr Arg His Gly Val Phe Val Glu Gln
                25                  30

Leu Gly Trp Lys Leu Pro Ser Ala Ser Glu
                35                  40

Gly Phe Glu Arg Asp Gln Tyr Asp Arg Asp
                45                  50

Asp Thr Val Tyr Val Phe Ala Arg Asp Asp
                55                  60

Asp Gly Glu Ile Cys Gly Cys Ala Arg Leu
                65                  70

Leu Pro Thr Thr Arg Pro Tyr Leu Leu Lys
                75                  80

Glu Leu Glu Pro Thr Leu Val Ala Gln Asp
                85                  90

Met Pro Leu Pro Gln Ser Ala Ala Val Trp
                95                  100

Glu Leu Ser Arg Phe Ala Ala Asn Ala Glu
                105                 110

Asp Pro Ala Gly Gly Gly Asn Pro Ala Trp
                115                 120

Ala Val Arg Pro Met Leu Ala Ala Val Val
                125                 130

Glu Cys Ala Ala Arg Leu Gly Ala Lys Gln
                135                 140

Leu Ile Gly Val Thr Phe Leu Ser Met Glu
                145                 150

Arg Leu Phe Arg Arg Ile Gly Val His Ala
                155                 160

His Arg Ala Gly Pro Ala Gln Gln Ile Asp
                165                 170

Gly Arg Met Val Val Ala Cys Trp Ile Asp
                175                 180

Leu Asp Ala Gln Thr Leu Ala Ala Leu Asp
                185                 190

Leu Asp Pro Leu Leu Cys Ala Pro Pro Ala
                195                 200

Glu Ala Ala
```

<210> SEQ ID NO 22
<211> LENGTH: 206
<212> TYPE: PRT
<213> ORGANISM: B. pseudomallei DD503 bpmI2

<400> SEQUENCE: 22

-continued

```
Met Ile Asp Thr Thr Val Ile Ser Ala Ala
 1               5                   10

Gln Leu Asp Ser Thr Val Lys Ala Ala Leu
                15                  20

Gly Asn Tyr Arg Arg Ala Ile Phe Ile Glu
                25                  30

Lys Leu Gly Trp Pro Leu Pro Leu Val Asp
                35                  40

Gly Leu Glu Ile Asp Gln Phe Asp Arg Pro
                45                  50

Asp Thr Ile Tyr Val Val Gly Lys Thr Glu
                55                  60

Ser Gly Asp Ile Cys Gly Cys Ala Arg Leu
                65                  70

Leu Pro Thr Thr Arg Pro Tyr Leu Leu Gly
                75                  80

Glu Val Phe Pro Asp Leu Met Gly Asp Ala
                85                  90

Ala Pro Pro Cys Ser Ala His Val Trp Glu
                95                  100

Ile Ser Arg Phe Ser Ser Ser Ile Leu Ser
                105                 110

Gly Gly Pro Asp Ala Leu Arg Gln Ala His
                115                 120

Arg Asn Thr Arg Ile Leu Leu Ala Lys Ile
                125                 130

Val Arg Phe Ala Gln Ala Ala Gly Val Lys
                135                 140

Arg Leu Ile Thr Val Ser Pro Leu Ala Val
                145                 150

Glu Arg Leu Leu Asn Arg Leu Lys Val His
                155                 160

Ile His Arg Ala Gly Pro Pro Arg Leu Ile
                165                 170

Asp Gly Lys Pro Val Phe Ala Cys Gln Ile
                175                 180

Glu Val Asp Asp Ile Thr Leu Gln Ala Leu
                185                 190

Asp Ile Glu Pro Ala Ala Asp Ser Ala Ala
                195                 200

Gly Ala Leu Arg His Ser
                205


<210> SEQ ID NO 23
<211> LENGTH: 202
<212> TYPE: PRT
<213> ORGANISM: B. pseudomallei DD503 bpmI3

<400> SEQUENCE: 23

Met Ser Tyr Ile Ile Ala Gly Arg Leu Asn
 1               5                   10

Glu Leu Pro Pro His Val Gln Thr Asp Leu
                15                  20

Gly Ala Tyr Arg Tyr Asp Val Phe Val Arg
                25                  30
```

-continued

Arg Leu Gly Trp Thr Ile Ala Gly His Ser
35 40

Leu Asp Glu His Ala Glu Trp Asp Glu Phe
45 50

Asp Gly Pro Ser Thr Ile His Val Val Ala
55 60

Leu Asp Asp Ala Arg Glu Ile Cys Gly Tyr
65 70

Ala Arg Leu Leu Pro Thr Thr Gly Pro Tyr
75 80

Leu Leu Arg Asp Val Phe Ala His Leu Leu
85 90

Gly Ser Ser Pro Ala Pro Gln Ser Pro Ala
95 100

Val Trp Glu Met Ser Arg Phe Ala Ala Ser
105 110

Arg Arg Arg Arg Ser Ala Thr Glu Arg Glu
115 120

Pro Leu Gly Met Ala Phe Phe Pro Ser Val
125 130

Leu Thr Val Ala Ala Ser Leu Gly Ala Thr
135 140

Arg Val Val Gly Val Met Thr Pro Ser Ile
145 150

Glu Arg Leu Tyr Arg Arg Ser Gly Ile Ala
155 160

Leu His Arg Leu Gly Asn Ala Met Pro Gly
165 170

Ala Gly Gly Ser Leu Ser Ala Cys Ser Ile
175 180

Asp Leu Pro Arg Leu Ala Phe Ala Pro Leu
185 190

Gly Arg Lys Gln Cys Ala Ala Cys Leu Ala
195 200

Met His

<210> SEQ ID NO 24
<211> LENGTH: 239
<212> TYPE: PRT
<213> ORGANISM: B. pseudomallei DD503 bpmR1

<400> SEQUENCE: 24

Met Glu Leu Arg Trp Gln Asp Ala Tyr Leu
1 5 10

Gln Phe Ser Ala Ala Glu Asn Glu Gln Gln
15 20

Leu Phe Gln Gln Ile Ala Ala Tyr Thr Lys
25 30

Arg Leu Gly Phe Glu Tyr Cys Cys Tyr Gly
35 40

Ile Arg Val Pro Leu Pro Ile Ser Lys Pro
45 50

Val Val Ala Ile Phe Asp Thr Tyr Pro Asn
55 60

-continued

Gly Trp Met Glu Arg Tyr Gln Glu Met Asn
65 70

Tyr Leu Glu Val Asp Pro Thr Val Arg Glu
75 80

Gly Ala Leu Ser Ser Asn Met Ile Val Trp
85 90

Pro Glu Ala Ser Ala Ser Asp Ala Thr Thr
95 100

Leu Trp Ser Asp Ala Arg Asp His Gly Leu
105 110

Ala Val Gly Val Ala Gln Ser Ser Trp Ala
115 120

Ser Arg Gly Val Phe Gly Leu Leu Thr Ile
125 130

Ala Arg His Thr Asp Arg Leu Thr Ser Ala
135 140

Glu Ile Asn His Leu Thr Leu Gln Ala Asn
145 150

Trp Leu Ala Asn Met Ser His Ser Leu Met
155 160

Ser Arg Phe Leu Val Pro Lys Leu Ala Pro
165 170

Glu Ser Gly Val Ala Leu Thr His Arg Glu
175 180

Arg Glu Val Leu Cys Trp Thr Gly Glu Gly
185 190

Lys Thr Ala Cys Glu Ile Gly Gln Ile Leu
195 200

Ser Ile Ser Glu Arg Thr Val Asn Phe His
205 210

Val Asn Asn Ile Leu Asp Lys Leu Gly Ala
215 220

Thr Asn Lys Val Gln Ala Val Val Lys Ala
225 230

Ile Ala Met Gly Leu Ile Asp Ala Pro
235

<210> SEQ ID NO 25
<211> LENGTH: 236
<212> TYPE: PRT
<213> ORGANISM: B. pseudomallei DD503 bpmR2

<400> SEQUENCE: 25

Met Glu Met His Asp Phe Leu Gln Phe Trp
1 5 10

Leu Asn Glu Phe Ser Arg Ser Glu Asn Pro
15 20

Gln His Val Ile Ser Val Leu Thr Arg Ala
25 30

Ala Ala Thr Leu Gly Tyr Glu Tyr Ala Ala
35 40

Tyr Gly Met Arg Arg Pro Phe Pro Ile Ser
45 50

Asn Pro Pro Ile Leu Met Val Ser Asn Tyr

-continued

```
                55                  60

Pro Ala Arg Trp Gln Glu Arg Tyr Ile Glu
                65                  70

Ala Arg Phe Ala Asn Ile Asp Gly Ala Val
                75                  80

Lys Ala Ala Leu Gly Ser Asp Arg Pro Val
                85                  90

Thr Trp Ser Ala Pro Ala Asn Ala Ser Lys
                95                 100

Ser Ala Phe Trp Ala Glu Ala Leu Ser Phe
               105                 110

Gly Ile Ala His Gly Trp Ser Ser Ala Ser
               115                 120

Arg Gly Ala Asp Gly Ala Ile Gly Val Leu
               125                 130

Thr Leu Ser Arg Thr Gln Asp Pro Ile Asp
               135                 140

Thr Ala Glu Lys Phe Arg Asn Glu Ser Ile
               145                 150

Val His Trp Leu Ala Asn Val Ala His Ala
               155                 160

Ser Met Ala Pro Phe Leu Pro Ala Ala Asp
               165                 170

Glu Phe Asp Pro Asp Leu Thr Arg Arg Glu
               175                 180

Thr Asp Val Leu Lys Trp Thr Ala Asp Gly
               185                 190

Lys Thr Ala Tyr Glu Ile Ala Leu Ile Leu
               195                 200

Ser Ile Ser Glu Ser Thr Val Asn Phe His
               205                 210

Val Lys Asn Ile Val Ser Lys Leu Gly Ser
               215                 220

Thr Asn Lys Ile Gln Ala Val Ala Lys Ala
               225                 230

Ala Leu Met Gly Met Leu
               235


<210> SEQ ID NO 26
<211> LENGTH: 230
<212> TYPE: PRT
<213> ORGANISM: B. pseudomallei DD503 bpmR3

<400> SEQUENCE: 26

Met Leu Ser Ala Ala Leu Pro Glu Ser Arg
 1               5                  10

Asp Val Arg Thr Leu Val Glu Thr Phe Arg
                15                  20

Gln Ala Ala Leu Gln Ile Gly Tyr Gln His
                25                  30

His Ala Ile Val Glu Leu Ser Gly Ala Ser
                35                  40

His Pro Ala Ser Ile Asp Val Val Ser Leu
                45                  50
```

-continued

His Tyr Pro Ser Glu Trp Val Glu His Tyr
55 60

Thr Arg Asn Asp Tyr Phe Ala Ile Asp Pro
65 70

Val His Arg Ala Ala Phe Arg Tyr Ser Thr
75 80

Pro Phe Ser Trp Asn Asp Val Ala Thr Ala
85 90

Asn Leu Arg Glu Arg His Leu Leu Met Glu
95 100

Ala Glu Asp Ala Gly Leu Asp Asn Gly Ile
105 110

Ser Ile Pro Leu His Gln Pro Leu Gly Arg
115 120

Val Leu Leu Val Ser Leu Ser Gly Thr Ala
125 130

Pro Thr His Asp Ala Asp Ala Lys Trp Arg
135 140

Asn Ala Tyr Leu Leu Gly Met Gln Phe Asn
145 150

Leu Gln Phe Gln Ser Met Arg Thr Cys Arg
155 160

Pro Ile Pro Pro Ser Val His Leu Thr Asp
165 170

Arg Glu Gln Met Cys Leu Thr Trp Val Ala
175 180

Arg Gly Lys Ser Ser Trp Val Ile Ala Asn
185 190

Met Leu Asp Ile Ser Lys Tyr Thr Val Asp
195 200

Phe His Ile Glu Asn Ala Met Glu Lys Leu
205 210

Asn Thr Arg Ser Arg Thr Phe Ala Ala Val
215 220

Lys Ala Thr Arg Gln Glu Leu Ile Phe Pro
225 230

<210> SEQ ID NO 27
<211> LENGTH: 294
<212> TYPE: PRT
<213> ORGANISM: B. pseudomallei DD503 bpmR4

<400> SEQUENCE: 27

Met Ala Arg Thr Arg Arg Gly Ala Ser Glu
1 5 10

Ser Arg Arg Ser Ala Arg Ala Gly Ala Ile
15 20

Ala Ala Arg Pro Ala Phe Arg Ala Arg Arg
25 30

Thr Gly Gly Ser Pro Arg Gly Arg Ala Gln
35 40

Pro Leu Ala Arg Gly Gly Gly Ala Arg Ser
45 50

Asp Gln Pro Ala Arg Arg Cys Asp Asp Asp
55 60

-continued

Arg Leu Arg Ala Val Val Arg Ala Tyr Leu
65 70

Ala Cys Gly Val Arg Gln Met Lys His Asp
75 80

Arg Ala Leu Arg Asp Ala Glu Asn Leu Arg
85 90

Asp Phe Pro Arg Arg Leu Ala Ala Pro Arg
95 100

Pro Leu Gln Arg Phe Ala Leu Ala Arg Gly
105 110

Gln Ile Ala Arg Ala Leu Pro Ser Glu Pro
115 120

Ala Ile Glu Gln Leu Val His Arg Arg Val
125 130

His Glu Ala Arg Glu Gln Leu Arg Gln Ala
135 140

Gln Gln Pro Gln Tyr Val Ala Arg Val Val
145 150

Leu Glu Arg Ile Val Gly Arg His Ala Glu
155 160

His Ala Asp Arg Ala Ala Ala Ile Val Asn
165 170

Gly Ala Thr Glu Pro Val Asp Glu Ala Val
175 180

Arg Phe Arg Leu Val Ala His Glu Leu Arg
185 190

Ala Ala Gly Arg Ile Glu Val Val Val Pro
195 200

Asp Glu Arg His Gly Pro Ala Pro Ala Met
205 210

Leu Asn Asp Gly Ile Asp Arg Gln Val Val
215 220

Gly Gly Val Val Ala Gln Pro Pro Leu Gly
225 230

Arg Lys Ser Val Glu His Ala Ala Ala Arg
235 240

Arg Arg Ala Gly Asp Leu Met Pro Val Arg
245 250

Glu Ile Leu Glu Ala Gln Leu Ala Asn Val
255 260

Ile Arg Arg Leu Leu Lys Glu Ala Leu Leu
265 270

Asn Ser Arg Val Gln Asn Phe Val Lys Arg
275 280

Thr Asn Gly Gln Ala Phe Glu His Arg Thr
285 290

Ala Gln Leu Lys

<210> SEQ ID NO 28
<211> LENGTH: 241
<212> TYPE: PRT
<213> ORGANISM: B. pseudomallei DD503 bpmR5

<400> SEQUENCE: 28

-continued

```
Met Arg Ala Ala Met Gly Asn Trp Ala Glu
 1               5                  10

Asp Leu Leu Ala Gly Leu Asp Ser Ala Arg
                15                  20

Ser Glu Glu Glu Ala Phe Arg Ser Val Glu
                25                  30

Thr Ala Ala Ala Ala Leu Asp Phe Glu Tyr
                35                  40

Cys Ala Tyr Gly Leu Arg Val Pro Trp Pro
                45                  50

Leu Ser Arg Pro Arg Ile Glu Thr Arg Ser
                55                  60

Asn Phe Pro Glu Gln Trp Lys Arg Arg Tyr
                65                  70

Val Glu Ala Gly Phe Leu Asp Val Asp Pro
                75                  80

Ile Leu Ala His Gly Arg Arg Ser Gln Gln
                85                  90

Pro Val Val Leu Ala Glu Thr Leu Phe Ala
                95                 100

Ser Ala His Gln Met Trp Val Glu Ala Gln
               105                 110

Ser Phe Gly Leu Arg Phe Gly Trp Ala Gln
               115                 120

Ser Ser Phe Asp Ala Tyr Gly Gly Met Gly
               125                 130

Met Leu Ala Leu Val Arg Ser Cys Glu Pro
               135                 140

Val Thr Ala Ala Glu Leu Asp Ala Lys Glu
               145                 150

Tyr Arg Met Arg Trp Leu Val Arg Thr Ala
               155                 160

His Ala Ala Leu Gly Arg Met Met Leu Pro
               165                 170

Lys Leu Met Ala Asp Pro Glu Arg Gly Leu
               175                 180

Thr Glu Arg Glu Val Glu Val Leu Lys Trp
               185                 190

Ala Ala Asp Gly Lys Thr Ser Gly Glu Ile
               195                 200

Ser Lys Ile Leu Ala Ile Ser Val Asp Thr
               205                 210

Val Asn Phe His Val Lys Asn Ala Ile Leu
               215                 220

Lys Leu Arg Thr Ala Asn Lys Thr Ala Ala
               225                 230

Val Val Arg Ala Ala Met Leu Gly Leu Leu
               235                 240

Ser
```

<210> SEQ ID NO 29
<211> LENGTH: 22
<212> TYPE: DNA

-continued

<213> ORGANISM: Artificial sequence
<220> FEATURE:
<223> OTHER INFORMATION: designed primer

<400> SEQUENCE: 29
ccgcgacgac gacggggaaa tc 22

<210> SEQ ID NO 30
<211> LENGTH: 23
<212> TYPE: DNA
<213> ORGANISM: Artificial sequence
<220> FEATURE:
<223> OTHER INFORMATION: designed primer

<400> SEQUENCE: 30
tcgatccagc acgcgacgac cat 23

<210> SEQ ID NO 31
<211> LENGTH: 24
<212> TYPE: DNA
<213> ORGANISM: Artificial sequence
<220> FEATURE:
<223> OTHER INFORMATION: designed primer

<400> SEQUENCE: 31
ataagcgccg cgcaactgga ttcc 24

<210> SEQ ID NO 32
<211> LENGTH: 24
<212> TYPE: DNA
<213> ORGANISM: Artificial sequence
<220> FEATURE:
<223> OTHER INFORMATION: designed primer

<400> SEQUENCE: 32
caggatcgcc gtattgcggt gagc 24

<210> SEQ ID NO 33
<211> LENGTH: 24
<212> TYPE: DNA
<213> ORGANISM: Artificial sequence
<220> FEATURE:
<223> OTHER INFORMATION: designed primer

<400> SEQUENCE: 33
tcgcgggccg attgaacgaa ctgc 24

<210> SEQ ID NO 34
<211> LENGTH: 24
<212> TYPE: DNA
<213> ORGANISM: Artificial sequence
<220> FEATURE:
<223> OTHER INFORMATION: designed primer

<400> SEQUENCE: 34
gagcgacgcg gccaccgtga gcac 24

<210> SEQ ID NO 35
<211> LENGTH: 24
<212> TYPE: DNA
<213> ORGANISM: Artificial sequence
<220> FEATURE:
<223> OTHER INFORMATION: designed primer

<400> SEQUENCE: 35
cggcttcgaa tattgctgct atgg 24

-continued

<210> SEQ ID NO 36
<211> LENGTH: 24
<212> TYPE: DNA
<213> ORGANISM: Artificial sequence
<220> FEATURE:
<223> OTHER INFORMATION: designed primer

<400> SEQUENCE: 36
gagaaaacgg ctcatcagcg agtg 24

<210> SEQ ID NO 37
<211> LENGTH: 23
<212> TYPE: DNA
<213> ORGANISM: Artificial sequence
<220> FEATURE:
<223> OTHER INFORMATION: designed primer

<400> SEQUENCE: 37
agcgaccggc ccgtgacctg gag 23

<210> SEQ ID NO 38
<211> LENGTH: 23
<212> TYPE: DNA
<213> ORGANISM: Artificial sequence
<220> FEATURE:
<223> OTHER INFORMATION: designed primer

<400> SEQUENCE: 38
cggcctgtat cttgttcgtg gac 23

<210> SEQ ID NO 39
<211> LENGTH: 24
<212> TYPE: DNA
<213> ORGANISM: Artificial sequence
<220> FEATURE:
<223> OTHER INFORMATION: designed primer

<400> SEQUENCE: 39
agacgtcgtc tcgctgcact atcc 24

<210> SEQ ID NO 40
<211> LENGTH: 24
<212> TYPE: DNA
<213> ORGANISM: Artificial sequence
<220> FEATURE:
<223> OTHER INFORMATION: designed primer

<400> SEQUENCE: 40
acccacgtga ggcacatctg ttcg 24

<210> SEQ ID NO 41
<211> LENGTH: 24
<212> TYPE: DNA
<213> ORGANISM: Artificial sequence
<220> FEATURE:
<223> OTHER INFORMATION: designed primer

<400> SEQUENCE: 41
ggcgttcgac agatgaaaca cgac 24

<210> SEQ ID NO 42
<211> LENGTH: 24
<212> TYPE: DNA
<213> ORGANISM: Artificial sequence
<220> FEATURE:

-continued

```
<223> OTHER INFORMATION: designed primer

<400> SEQUENCE: 42

gctcatctgg cacgacgacc tcta                                    24


<210> SEQ ID NO 43
<211> LENGTH: 22
<212> TYPE: DNA
<213> ORGANISM: Artificial sequence
<220> FEATURE:
<223> OTHER INFORMATION: designed primer

<400> SEQUENCE: 43

cgcgtgccgt ggccgctgtc ca                                      22


<210> SEQ ID NO 44
<211> LENGTH: 23
<212> TYPE: DNA
<213> ORGANISM: Artificial sequence
<220> FEATURE:
<223> OTHER INFORMATION: designed primer

<400> SEQUENCE: 44

ccgcgctccg ggtccgccat cag                                     23
```

GLANDERS/MELIODOSIS VACCINES

This application claims the benefit of priority under 35 U.S.C. 119(e) from U.S. application Ser. No. 60/396,257 filed on Jul. 15, 2002.

INTRODUCTION

*Burkholderia mallei*, the etiologic agent of glanders disease is a gram-negative, oxidase positive, nonmotile bacillus that is an obligate animal pathogen (DeShazer, D and D. M. Wang, 2002, New Insights into an Old Disease. In L. Lindler et al. eds., Biological Weapons Defense: Principes and Mechanisms for Infectious Diseases Counter-Bioterrorism. The Humana Press Inc.). The natural hosts of *B. mallei* are horses, donkeys, and mules (solipeds) while humans are considered an incidental host (DeShazer and Wang, 2002, supra). Until the early $20^{th}$ century, and the development of motorized transportation, glanders disease was prevalent worldwide (DeShazer and Wang, 2002, supra). With the requirement of quaratinement of imported animals, no naturally occurring cases of glanders have been reported in the United States since 1934 (DeShazer and Wang, 2002, supra). Human glanders is uncommon, and occasionally occurs in individuals (veterinarians, slaughter house workers, and laboratory scientists) whose occupation puts them at risk (Steele, J. H., 1979, In: Steele J H, ed. CRC Handbook Series in Zoonoses. Boca Raton, Fla.: CRC Press, 339-362). In solipeds, two distinctive forms of glanders may arise, chronic (common in horses) and acute (observed in mules and donkeys). Symptoms of acute glanders include weight loss, difficulty breathing, and elevated temperature. In contrast, horses with chronic glanders may exhibit pulmonary, cutaneous (farcy), and respiratory symptoms. Human acute glanders is characterized by fever, fatigue, and inflammation and nodule formation on the face and peripheral limbs (DeShazer and Wang, 2002, supra). Symptoms of chronic glanders in humans consist of swollen lymph nodes, ulcerating nodules in the alimentary and respiratory tracts, and numerous subcutaneous abscesses (DeShazer and Wang, 2002, supra).

*Burkholderia pseudomallei*, the causative agent of melioidosis, inflicts high incidences of human pneumonia and deadly bacteremia in endemic areas including Southeast Asia and northern Australia (Woods, D. E. et al., 1999, Microbes Infect. 2, 157-162; Dance, D. A., 2002, Melioidosis, Curr. Opin. Infect. Dis. 2, 127-132). Interestingly, recent studies have successfully isolated *B. pseudomallei* from both the environment and humans in areas of Europe, Africa, the Middle East, and central and South America (Woods, D E et al., 1999, supra). *B. pseudomallei* is a gram-negative soil saprophyte and is a common inhabitant of surface waters and soil (Ulett, G C et al., 2001, Microbes Infect. 3, 621-631). Disease in humans normally occurs in individuals who are frequently exposed to contaminated surface water and soil, in particular rice farmers in Thailand and the Aboriginal people in Australia (Ulett et al., 2001, supra). Several underlying host conditions including diabetes, renal complications, and alcoholism are additional risk factors for contracting *B. pseudomallei* (Ulett et al., 2001, supra). Symptoms of melioidosis are discrete and may include acute or chronic pneumonia, acute septicemia and even latent infections that can persist for several years (Ulett et al., 2001, supra).

Aerosol exposure to *B. mallei* and *B. pseudomallei* results in sinus cavity colonization, followed by dissemination into the blood stream and peripheral organs in animal models of infection. Because biofilm maturation is probably important for sinus colonization, mutants impaired in biofilm progenesis may be hindered in their aerosol pathogenicity and may give insight into the unique aspects of these pneumonic diseases.

The bacterial quorum sensing cascade has been shown to be critical for regulating many cell-density dependant processes, including biofilm maturation. The quorum gene systems found in numerous gram-negative bacteria are sophisticated cell-cell signaling pathways that allow a microorganism to detect and respond at the transcriptional level to fluctuating environmental conditions (Fuqua, C. et al., 2001, Annu. Rev. Genet. 35, 439-468). Briefly, quorum systems operate using synthase enzymes (AHS) that produce small signaling molecules termed N-acyl-homoserine lactones (AHL), which bind to transcriptional regulatory proteins (LuxR) and activate or repress gene expression. Often, bacterial species possess multiple quorum networks and the interaction between the diffrent systems adds complexity and flexibility to gene expression.

This ability to transduce intracellular signals, termed quorum-sensing, involves the synthesis and accumulation of AHLs (Fuqua, C. et al., 2001, supra). AHLs are secreted into the extracellular medium and diffuse back into the cell when a high concentration has been reached. AHL biosynthesis is enzymatically mediated by the LuxI family of proteins and a single LuxI may produce multiple AHLs with varying side chain lengths (Fuqua, C. et al., 2001, supra). LuxR proteins respond to AHLs in a concentration dependent manner through the binding of the signal molecule. This protein interaction induces conformational changes and multimerization of the enzyme, which in turn induces or represses target gene expression (Fuqua, C. et al., 2001, supra). In animal and plant pathogens, coordinated gene expression, in particular alleles encoding proteins needed for virulence, allows microorganisms to elicit an overwhelming attack before host cells can mount an effective defense (Fuqua, C. et al., 2001, supra).

In *Pseudomonas aeruginosa*, two thoroughly characterized quorum networks have been analyzed at the genetic and biochemical levels and consist of the lasIR and rhlIR systems (Fuqua, C. et al., 2001, supra). Collectively, these quorum networks direct the synthesis of N-3-oxodo-decanoyl homoserine lactone (LasI) and N-butyryl-homoserine lactone (RhlI) and encode the transcriptional regulators for elastase (LasR) and rhamnolipid (RhlR) biosynthesis (Fuqua, C. et al., 2001, supra). Disruption of the *P. aeruginosa* lasIR and rhlIR systems significantly reduces the virulence in multiple animal models including acute and chronic lung infections in neonatal mice and adult rats (Smith, R. S. et al., 2002, J. Bacteriol. 184, 1132-1139). Additionally, several investigations have demonstrated that N-3-oxodo-decanoyl homoserine lactone accumulation in vitro and in vivo promotes the induction of numerous inflammatory mediators that result in tissue destruction and subsequent dissemination of *P. aeruginosa* to peripheral organs (Smith, R. S. et al., 2002, supra).

Lewenza et al. and Conway et al. recently identified functional quorum-sensing networks in *Burkholderia cepacia* and *Burkholderia vietnamiensis* (Lewenza, S. et al., 1999, J. Bacteriol. 181, 748-756; Lewenza, S. and P. A. Sokol 2001, J. Bacteriol. 183, 212-218; Conway, B. and E. P. Greenberg, 2002, *J. Bacteriol.* 184, 1187-1191). The *B. cepacia* quorum system is comprised of the cepIR loci. CepI directs the biosynthesis of N-octanoyl-homoserine lactone ($C_8$-HSL) and N-hexanoyl-homoserine lactone ($C_6$-HSL) (Lewenza et al., 1999, supra). Mutational analysis of the cepIR system demonstrated that CepR negatively regulated ornibactin synthesis and positively induced protease and $C_8$-HSL biosynthesis (Lewenza and Sokol, 2001, supra). These findings indicate that quorum sensing in *B. cepacia* positively and negatively regulates potential virulence factors using a cell density mechanism.

In an effort to identify quorum alleles encoded by both *B. mallei* and *B. pseudomallei*, an in silico approach was pursued that used the LasIR, RhlIR, and the CepIR amino acid sequences to search the *B. pseudomallei* K96243 and the *B. mallei* ATCC 23344 genomes for quorum sensing homologues.

BLAST search revealed that the *B. pseudomallei* genome encodes three AHS genes (bpmI1, bpmI2, and bpmI3) and five transcriptional regulators (bpmR1, bpmR2, bpmR3, bpmR4, and bpmR5) belonging to the LuxR family of proteins. In contrast, *B. mallei* contains two AHS genes (bmaI1 and bmaI2) and four LuxR homologues (bmaR1, bmaR3, bmaR4, bmaR5). The relative genetic organization of these complex quorum sensing operons are shown in FIG. 1. Interestingly, *B. mallei* is lacking the entire bpmIR2 locus and the flanking open reading frames (orf). The genes encoded within these operons show an interesting arrangement relative to other characterized quorum systems in gram-negative bacteria. Usually, the AHS and LuxR genes are arranged in an uninterrupted tail-to-tail orientation. None of the identified loci display this arrangement. Further, there are LuxR genes (bmaR4, bmaR5, bpmR4, and bpmR5) encoded by both *B. mallei* and *B. pseudomallei* that are orphaned for a cognate AHS. Typically, both genes are found together and interact with each other. Based upon the in silico recovered quorum alleles, we selected oligonucleotide primers for the amplification of an internal fragment of approximately 400 bp in each gene (Table 2). We cloned the internal fragments following amplification using a topoisomerase mediated method. The internal fragments were subcloned into a suicide plasmid bearing a gentamycin resistance marker for mobilization via *E. coli* into *B. mallei* and *B. pseudomallei* (Sambrook, J. et al., 1989, Molecular Cloning: a Laboratory Manual, $2^{nd}$ ed. Cold Spring Harbor Laboratory Press, Cold Spring Harbor, N.Y.; Simon, R. et al., 1983, Bio/technology 1, 784-791; DeShazer, D. et al., 2001, Microb. Pathog. 30, 253-269). A single crossover event between the internal gene fragment and the bacterial chromosome would generate a merodiploid, disrupt the targeted gene and give the recipient a gentamycin resistant phenotype. Merodiploids were constructed in each of the *B. mallei* and *B. pseudomallei* quorum alleles and the resulting strains were phenotypically characterized in vivo (see Table 1 for bacteria and strains used in this study). The *B. pseudomallei* allele for each gene to be disrupted was used in the construction of the insertional mutagenesis cassette. Utilization of this strategy allowed the generation of mutants with the smallest number of mutagenesis cassette clones.

Interestingly, both the GB8::bpmI1 and GB8::bpmI3 mutants were avirulent even though they both produced a capsule. To date the only definitive virulence factor associated with pathogenicity of *B. mallei* is extracelllar capsule (DeShazer, D. et al., 2001, supra). All of the *B. mallei* quorum sensing mutants tested in this study produce capsule even those with reduced virulence. This is of significant importance indicating that this study has identified novel and previously unknown regulators of virulence and virulence gene expression.

The reduction in the ability of all the *B. mallei* quorum sensing mutans, in particular, GB8::bpmI3 and GB8::bpmI1, to colonize the spleen, liver, and lungs of aerosolized BALB/c mice indicated that quorum sensing plays a pivotal role in the pathogenicity of *B. mallei* in vivo. Exposure of animals to GB8::bpmI3 mutants prior to challenge protected approximately 40% of animals over a 21 day period while all unvaccinated animals perished within 3 days. There are no published reports showing the efficacy of a subunit or live attenuated strain of *B. mallei* providing any protection against an aerosol challenge with wild-type.

This was an unexpected result. Given that the capsule mutants were avirulent, we expected that they would protect. However, they do not. In retrospect, it seems that the quorum mutants retain enough vigor to activate the host immune system while the capsule mutants were simply cleared. The majority of clinical data previously reported suggests that the capsule and LPS would make a good vaccine, but all preparations of components to date have failed to yield sterile immunity following an aerosol challenge.

SUMMARY OF THE INVENTION

We have cloned and characterized 8 previously unknown quorum genes from *B. pseudomallei* DD503, and using this information were able to clone and characterize 6 new quorum genes from *B. mallei* ATCC 23344. We have shown that disruption of genes with the bmaIR locus results in avirulent strains of *B. mallei* and that some of these strains can effectively be used as a vaccine against glanders disease.

Therefore, it is one object of the present invention to provide a DNA fragment encoding each of the *B. mallei* AHS and AHS transcriptional regulators (LuxR) quorum genes, bmaI1 (612 bp, SEQ ID NO:1), bmaI3 (609 bp, SEQ ID NO:2), bmaR1 (720 bp, SEQ ID NO:3) bmaR3 (609 bp, SEQ ID NO:4), bmaR4 (660 bp, SEQ ID NO:5), and bmaR5(726 bp, SEQ ID NO:6).

It is another object of the present invention to provide a DNA fragment encoding each of the *B. pseudomallei* quorum genes, bpmI1 (612 bp, SEQ ID NO:7), bpmI2 (621 bp, SEQ ID NO:8), bpmI3 (609 bp, SEQ ID NO:9), bpmR1 (720 bp, SEQ ID NO:10), bpmIR2 (711 bp, SEQ ID NO:11), bpmR3 (693 bp, SEQ ID NO:12), bpmR4 (885 bp, SEQ ID NO:13), bpmR5 (726 bp, SEQ ID NO:14).

It is another object of the present invention to provide the DNA fragments mentioned above in a recombinant vector. When the vector is an expression vector, the Burkholderia proteins encoded by the DNA fragments are produced. The DNA fragments are useful as a diagnostic agent, an agent for preparation of the protein which it encodes, and as a therapeutic agent. Specifically, the bpmIR2 genes, which *B. mallei* lacks, will provide an ideal diagnostic target to distinguish *B. pseudomallei* from *B. mallei.*

It is another object of the invention to provide an amino acid sequence encoded by the DNA sequences above.

It is a further object of the present invention to provide a host cell transformed with the above-described recombinant DNA construct.

It is another object of the present invention to provide a method for producing the above-mentioned AHSs and AHS transcriptional regulators encoded by the DNA fragments above, the method comprising culturing a host cell under conditions such that the above-described DNA fragment is expressed and the encoded protein is thereby produced, and isolating the protein for use as a reagent, for example for screening of drugs and inhibitors of AHS, for drugs and inhibitors that compete or inhibit the binding of the AHS to the LuxR homologues, for drugs and inhibitors of the LuxR transcriptional regulators, or for inhibiting the AHS quorum sensing operon.

It is a further object of the present invention to provide an antibody to the above-described recombinant proteins.

It is yet another object of the present invention to provide a method for detecting AHS in a sample comprising:

(i) contacting a sample with antibodies which recognize AHS; and (ii) detecting the presence or absence of a complex formed between AHS and antibodies specific therefor.

It is yet another object of the present invention to provide a method for detecting AHS transcriptional regulator in a sample comprising:

(i) contacting a sample with antibodies which recognize AHS transcriptional regulator; and (ii) detecting the presence or absence of a complex formed between AHS transcriptional regulator and antibodies specific therefor.

It is a further object of the present invention to provide a diagnostic kit comprising an antibody against AHS and ancillary reagents suitable for use in detecting the presence of AHS in a sample, e.g. tissue or serum from, mammals including humans, animals, birds, fish, plants and fungi, air, soil, or water.

It is yet another object of the present invention to provide a method for the detection of AHS, or LuxR transcription regulators in a sample using the polymerase chain reaction.

It is a further object of the present invention to provide a diagnostic kit comprising primers or oligonucleotides specific for AHS RNA or cDNA suitable for hybridization to AHS RNA or cDNA and/or amplification of AHS sequences and ancillary reagents suitable for use in detecting AHS RNA/cDNA in a sample.

It is yet another object of the present invention to provide a method for the detection of AHS in a sample which comprises assaying for the presence or absence of AHS RNA or cDNA in a sample by hybridization assays.

It is yet another object of the present invention to provide a method for reducing Burkholderia virulence by inhibiting the expression of one or more AHS in said cell. The inhibition can be at the DNA level by introducing mutations into the gene encoding one or more AHS, by inhibiting transcription of the gene, by inhibiting translation of the RNA encoding one or more AHS, or by inhibiting the function of one or more AHS.

It is yet another object of the present invention to provide a method for reducing Burkholderia virulence by inhibiting the expression of one or more LuxR transcriptional regulator in said cell. The inhibition can be at the DNA level by introducing mutations into one or more gene encoding one or more transcriptional regulator, by inhibiting transcription of the gene, by inhibiting translation of the RNA encoding a transcriptional regulator, or by inhibiting the function of one or more transcriptional regulator.

It is a further object of the present invention to provide Burkholderia strains containing one or more alteration in one or more AHS or LuxR quorum gene sequence. Such alteration can be insertions, deletions, or substitutions.

It is another object of the present invention to provide *B. mallei* or *B. pseudomallei* strains containing a non-revertable mutation within any of the AHS genes and/or LuxR gene for use in a vaccine composition.

It is yet another object of the present invention to provide a method and composition to elicit Burkholderia specific immune response in an individual comprising administering to the individual GB8::bpmI3 or a strain with a non-revertable mutation in bmaI3 in an amount sufficient to induce such a response.

It is another object of the present invention to provide a method for making an avirulent strain of *B. mallei* or *B. pseudomallei*, comprising disrupting one or more AHS gene and/or one or more LuxR gene.

It is further an object of the invention to provide an immunological composition for the protection of subjects against aerosolized glanders infection comprising *B. mallei* containing one or more disruption in one or more AHS gene and/or one or more LuxR gene allele, wherein said disruption is due to an insertion or deletion or substitution in the AHL synthase allele.

It is still another object of the present invention to provide a method for identifying downstream components or interacting proteins important for the virulence of *B. mallei* or *B. pseudomallei* activated by AHS or LuxR genes, by identifying genes expressed in the wild type Burkholderia but not in a mutant avirulent strain having a mutation in one or more AHS genes and/or one or more LuxR genes.

BRIEF DESCRIPTION OF THE DRAWINGS

These and other features, aspects, and advantages of the present invention will become better understood with reference to the following description and appended claims, and accompanying drawings.

DETAILED DESCRIPTION

Figure 1:
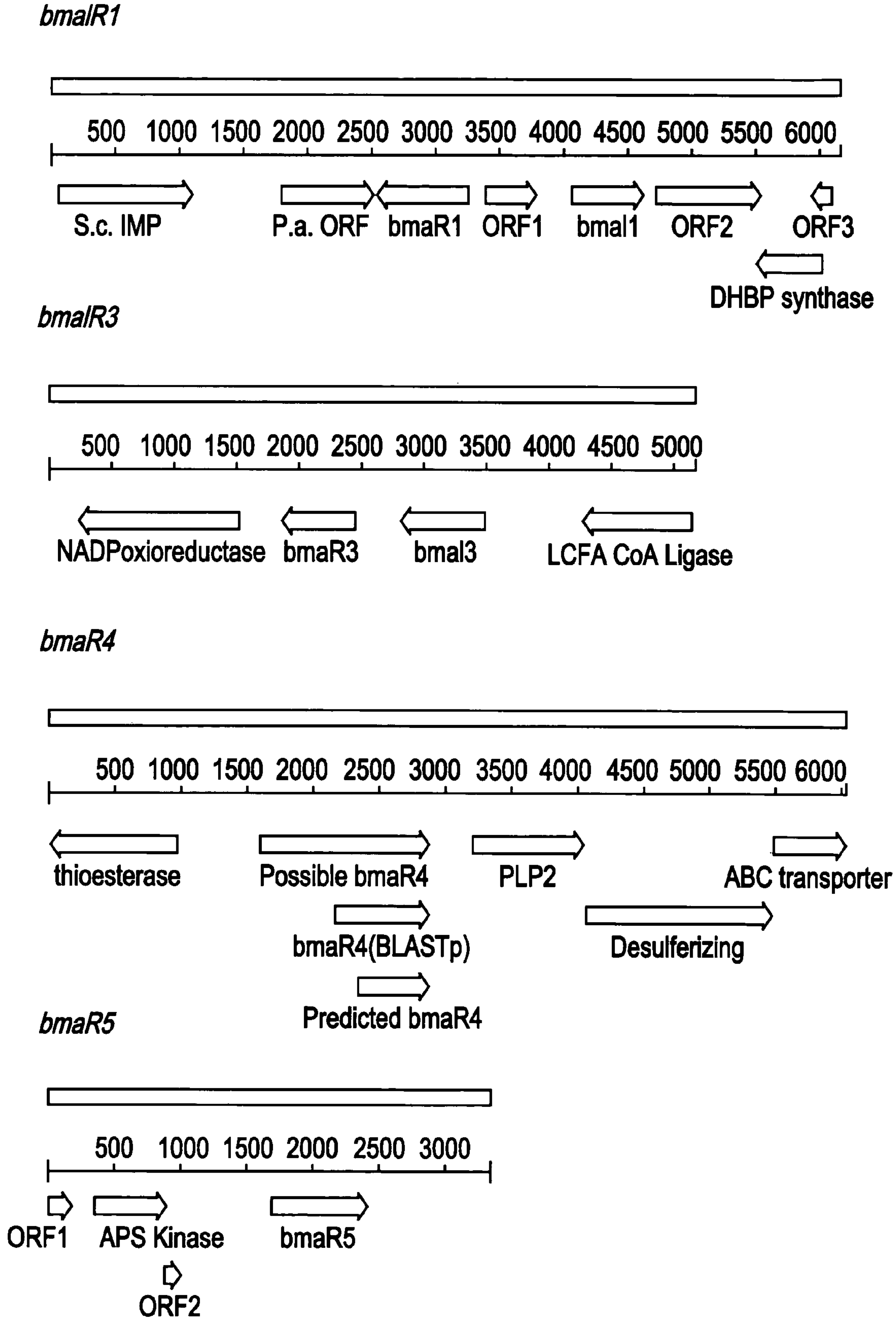
FIG. 1. Structural organization of the *B. mallei* ATCC 23344 quorum sensing network. The ASH genes are represented as bmaI1 and bmaI3 and the luxR homologues are labeled as bmaR1, bmaR3, bmaR4, and bmaR5. ORF depicts a potential open reading frame. The surrounding genes are putative orfs identified by performing tblastn searches.
Figure 2:
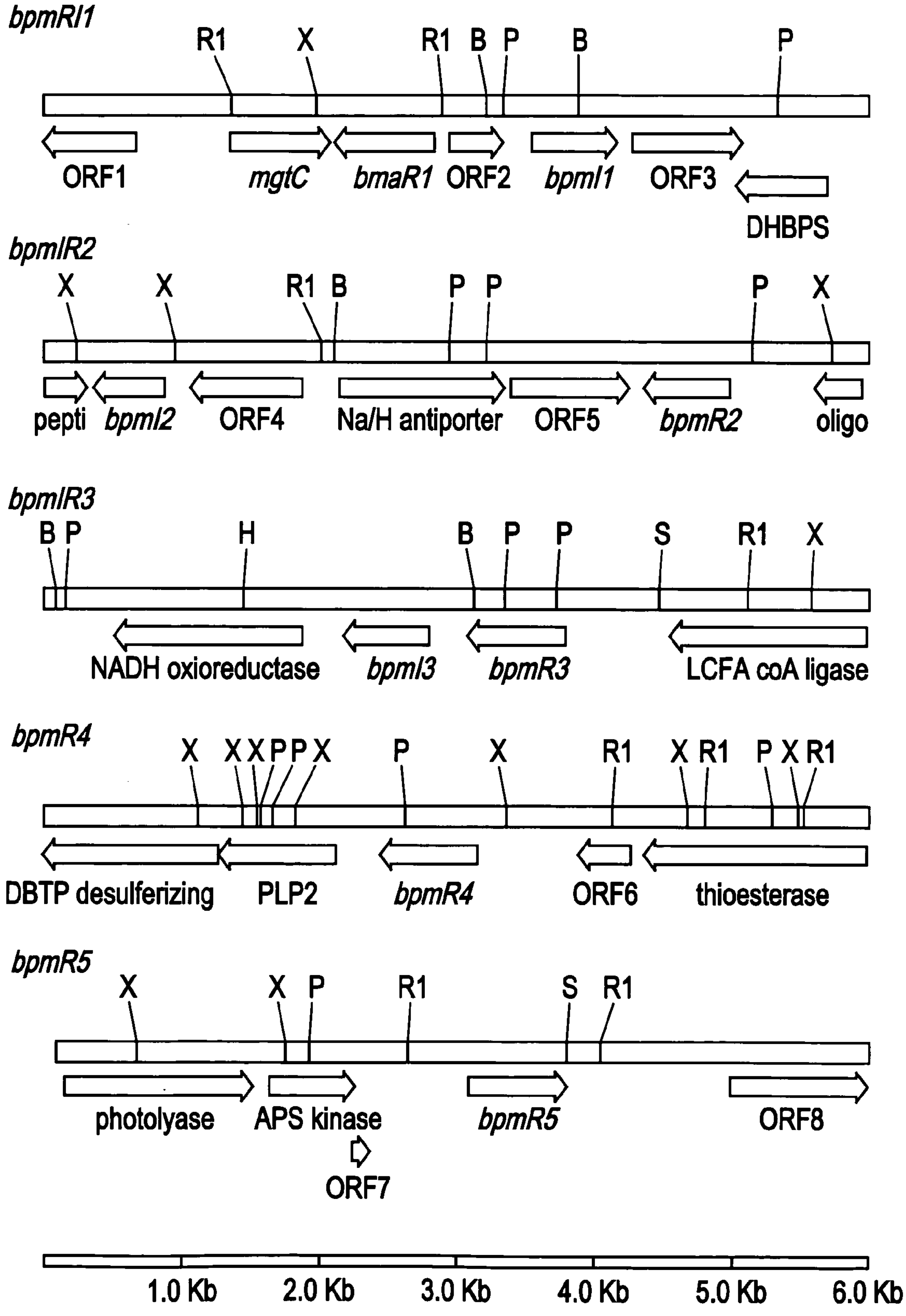
FIG. 2. Structural organization of the *B. pseudomallei* K96234 quorum sensing network. The ASH genes are represented as bpmI1, bpmI2 and bpmI3 and the luxR homologues are labeled as bmaR1, bmaR2, bmaR3, bmaR4, and bmaR5. ORF depicts a potential open reading frame. The surrounding genes are putative ORFs identified by performing tblastn searches.

In one embodiment, the present invention relates to DNA fragments which encode *B. mallei* AHS genes, bmaI1 (SEQ ID NO:1), and bmaI3 (SEQ ID NO:2) which are involved in the synthesis of N-acyl-homoserine lactones (AHL) and LuxR genes or DNA fragments which encode transcriptional regulatory proteins bmaR1 (SEQ ID NO:3), bmaR3 (SEQ ID NO:4), bmaR4 (SEQ ID NO:5), and bmaR5 (SEQ ID NO:6) which bind signals produced by AHS and activate or repress gene expression.

This invention further relates to DNA fragments encoding *B. pseudomallei* AHS genes, bpmI1 (SEQ ID NO:7), bpmI2 (SEQ ID NO:8), and bpmI3 (SEQ ID NO:9) and LuxR genes which encode transcriptional regulatory proteins bpmR1 (SEQ ID NO:10), bpmR2 (SEQ ID NO:11), bpmR3 (SEQ ID NO:12), bpmR4 (SEQ ID NO:13), and bpmR5 (SEQ ID NO:14).

In addition, this invention relates to the amino acid sequence of *B. mallei* AHS, BmaI1 (SEQ ID NO:15), and BmaI3 (SEQ ID NO:16) which are involved in the synthesis of N-acyl-homoserine lactones (AHL) and transcriptional regulatory response proteins BmaR1 (SEQ ID NO:17), BmaR3 (SEQ ID NO:18), BmaR4 (SEQ ID NO:19), and BmaR5 (SEQ ID NO:20). This invention further relates to the amino acid sequence of *B. pseudomallei* AHS, BpmI1 (SEQ ID NO:21), BpmI2 (SEQ ID NO:22), and BpmI3 (SEQ ID NO:23) and transcriptional regulatory response proteins BpmR1 (SEQ ID NO:24), BpmR2 (SEQ ID NO:25), BpmR3 (SEQ ID NO:26), BpmR4 (SEQ ID NO:27), and BpmR5 (SEQ ID NO:28).

Thus, one aspect of the invention provides an isolated nucleic acid molecule comprising a polynucleotide having a nucleotide sequence selected from (a) a nucleotide sequence comprising a sequence encoding a full length AHS polypeptide from *B. mallei* or *B. pseudomallei* having the sequence specified in SEQ ID NO:1-14, (b) a nucleotide sequence which encodes the complete amino acid sequence in SEQ ID NO:15-28.

In addition, isolated nucleic acid molecules of the invention include DNA molecules which comprise a sequence substantially different from those described above but which, due to the degeneracy of the genetic code, still encode the protein or fragments thereof. Of course, the genetic code and species-specific codon preferences are well known in the art. Thus, it would be routine for one skilled in the art to generate the degenerate variants described above, for instance, to optimize codon expression for a particular host (e.g., change codons in a human mRNA to those preferred by a bacterial host such as *E. coli*).

Nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

The present invention is further directed to nucleic acid molecules encoding portions or fragments of the nucleotide sequences described herein. Fragments include portions of the nucleotide sequence of SEQ ID NO:1-14 or at least 10 contiguous nucleotides in length selected from any two integers, one of which representing a 5' nucleotide position and a second of which representing a 3' nucleotide position, where the first nucleotide for each nucleotide sequence is position 1. That is, every combination of a 5' and 3' nucleotide position that a fragment at least 10 contiguous nucleotide bases in length or any integer between 10 and the length of an entire nucleotide sequence of the gene minus 1.

Further, the invention includes polynucleotides comprising fragments specified by size, in nucleotides, rather than by nucleotide positions. The invention includes any fragment size, in contiguous nucleotides, selected from intergers between 1—and the entire length of an entire nucleotide sequence minus 1. Preferred sizes include 20-50 nucleotides, 50-300 nucleotides useful as primers and probes. Regions from which typical sequences may be derived include but are not limited to, for example, regions encoding specific domains within said sequence, such as the region comprising the active domain of the enzyme, or the domain which binds the transcriptional regulatory protein.

In another aspect, the invention provides isolated nucleic acid molecules comprising polynucleotides which hybridize under stringent hybridization conditions to a polynucleotide sequence of the present invention described above, or a specified fragment thereof. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 g/ml denatured sheared salmon sperm DNA, followed by washing the filters in 0.1×SSC at about 65° C.

The sequences encoding the polypeptides of the present invention or portions thereof may be fused to other sequences which provide additional functions known in the art such as a marker sequence, or a sequence encoding a peptide which facilitates purification of the fused polypeptide, peptides having antigenic determinants known to provide helper T-cell stimulation, peptides encoding sites for post-tranlational modifications, or amino acid sequences which target the fusion protein to a desired location, e.g. a heterologous leader sequence.

The present invention further relates to variants of the nucleic acid molecules of the present invention, which encode portions, analogs or derivatives of the polypeptides. Variant may occur naturally, such as a natural allelic variant. By an "allelic variant" is intended one of several alternate forms of a gene occupying a given locus of a chromosome of an organism. Non-naturally occurring variants may be produced by known mutagenesis techniques. Such variants include those produced by nucleotide substitution, deletion, or addition of one or more nucleotides in the coding or noncoding regions or both. Alterations in the coding regions may produce conservative or nonconservative amino acid substitutions, deletions, or additions.

Nucleic acid molecules with at least 90-99% identity to any nucleic acid shown in any of SEQ ID NO:1-14 is another aspect of the present invention. These nucleic acids are included irrespective of whether they encode a polypeptide having AHS activity or AHS transcriptional regulator protein activity. By "a polypeptide having AHS activity" is intended polypeptides exhibiting activity similar, but not identical, to an activity of the AHS of the invention, as measured in the assays described below. By "a polypeptide having AHS transcriptional regulator activity" is intended polypeptides exhibiting activity similar, but not identical, to an activity of the transcriptional regulator of the invention, as measured in the assays described below. The biological acitivity or function of the polypeptides of the present invention are expected to be similar or identical to polypeptides from other organisms that share a high degree of structural identity/similarity. There are different strains of Burkholderia. The AHS and AHS transcriptional regulator genes of these different strains have not been sequenced. It would be expected that these proteins would have homology among different strains and that vaccination against one Burkholderia strain might afford cross protection to other Burkholderia strains.

In another embodiment, the present invention provides allelic variants wherein the gene has been altered for the purpose of reducing or eliminating activity of the gene product, i.e. the AHS or the AHS transcriptional regulator. Such negative allelic variants can be produced by the methods described by Moore et al. (Moore, R. A. et al., 1999, Antimicrob. Agents Chemother. Mar 43, 465-470). It is conceivable that a single derivative of *B. mallei* containing multiple deletions, for example in the AHS genes, bmaI3 and bmaI1, and the LuxR gene bmaR5, will display a combined phenotype that results in an extremely attenuated, or an avirulent strain of *B. mallei*. Such an a strain can be used in a vaccine composition as described below.

In another embodiment, the present invention relates to a recombinant DNA molecule that includes a vector and a DNA sequence as described above. The vector can take the form of a plasmid, phage, cosmid, YAC, eukaryotic expression vector such as a DNA vector, *Pichia pastoris*, or a virus vector such as for example, baculovirus vectors, retroviral vectors or adenoviral vectors, and others known in the art. The cloned gene may optionally be placed under the control of (i.e., operably linked to) certain control sequences such as promoter sequences, or sequences which may be inducible and/or cell type-specific. Suitable promoters will be known to a person with ordinary skill in the art. The expression construct will further contain sites for transcription initiation, termination and, in the transcribed region, a ribosome binding site for translation. Among the vectors preferred for use include pCR2.1-TOPO, pGSV3, to name a few. Introduction of the construct into the host cell can be effected by calcium phosphate transfection, electroporation, infection, and other methods known in the art and described in standard laboratory manuals such as Current Protocols in Molecular Biology, Ausubel, F. M. et al. (Eds), Wiley & Sons, Inc. All documents cited herein supra and infra are hereby incorporated in their entirety by referece thereto.

In a further embodiment, the present invention relates to host cells stably transformed or transfected with the above-described recombinant DNA constructs. The host cell can be prokaryotic (for example, bacterial), lower eukaryotic (for example, yeast or insect) or higher eukaryotic (for example, all mammals, including but not limited to rat and human). Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Please see e.g., Maniatis, Fitsch and Sambrook, Molecular Cloning; A Laboratory Manual (1982) or DNA Cloning, Volumes I and II (D. N. Glover ed. 1985) for general cloning methods. The DNA sequence can be present in the vector operably linked to a sequence encoding an IgG molecule, an adjuvant, a carrier, or an agent for aid in purification of the encoded protein, such as glutathione S-transferase, or a series of histidine residues also known as a histidine tag. The recombinant molecule can be suitable for transfecting eukaryotic cells, for example, mammalian cells and yeast cells in culture systems. *Saccharomyces cerevisiae, Saccharomyces carlsbergensis*, and *Pichia pastoris* are the most commonly used yeast hosts, and are convenient fungal hosts. Control sequences for yeast vectors are known in the art. Mammalian cell lines available as hosts for expression are known in the art and include many immortalized cell lines available from the American Type Culture Collection (ATCC), such as HEK293 cells, and NIH 3T3 cells, to name a few. Suitable promoters are also known in the art and include viral promoters such as that from SV40, Rous sarcoma virus (RSV), adenovirus (ADV), bovine papilloma virus (BPV), and cytomegalovirus (CMV). Examples of suitable promoting sequences for use with yeast hosts include the promoters for 3-phosphoglycerate kinase or other glycolic enzymes, such as enolase, glyceraldehyde-3-phosphate dehydrogenase, hexokinase, pyruvate decarboxylase, phosphofructokinase, glucose-6-phosphate isomerase, 3-phosphoglycerate. Mammalian cells may also require terminator sequences and poly A addition sequences; enhancer sequences which increase expression may also be included, and sequences which cause amplification of the gene may also be desirable. These sequences are known in the art. The transformed or transfected host cells can be used as a source of DNA sequences described above. When the recombinant molecule takes the form of an expression system, the transformed or transfected cells can be used as a source of the protein described below.

In another embodiment, the present invention relates to a AHS protein having an amino acid sequence corresponding SEQ ID NO:15, 16, 21, 22, and 23 or any allelic variation thereof or biologically active or biologically inactive derivative thereof. The present invention further relates to AHS transcriptional regulator protein having an amino acid sequence corresponding to SEQ ID NO:17-20, 24-28 or any allelic variation thereof or biologically active or biologically inactive derivative thereof.

A polypeptide or amino acid sequence derived from the amino acid sequences mentioned above, refers to a polypeptide having an amino acid sequence identical to that of a polypeptide encoded in the sequence, or a portion thereof wherein the portion consists of at least 2-5 amino acids, and more preferably at least 8-10 amino acids, and even more preferably at least 11-15 amino acids, or which is immunologically identifiable with a polypeptide encoded in the sequence.

A "biologically active derivative thereof" is a AHS or a AHS transcriptional regulator that is modified by amino acid deletion, addition, substitution, or truncation, or that has been chemically derivatized, but that nonetheless functions in the same manner as any protein of SEQ ID NO:15-28. For example, it is known that substitutions of aliphatic amino acids such as alanine, valine, and isoleucine with other aliphatic amino acids can often be made without altering the structure or function of a protein. Similarly, substitution of aspartic acid for glutamic acid, in regions other than the active site of an enzyme, are likely to have no appreciable affect on protein structure or function. The term "fragment" is meant to refer to any polypeptide subset. Fragments can be prepared by subjecting Burkholderia proteins to the action of any one of a number of commonly available proteases, such as trypsin, chymotrypsin or pepsin, or to chemical cleavage agents, such as cyanogen bromide. The term "variant" is meant to refer to a molecule substantially similar in structure and function to either the entire AHS or AHS transcriptional regulator or to a fragment thereof. A protein or peptide is said to be 'substantially similar' if both molecules have substantially similar amino acid sequences, preferably greater than about 80% sequence identity, or if the three-dimensional backbone structures of the molecules are superimposable, regardless of the level of identity between the amino acid sequences. Thus, provided that two molecules possess similar activity, they are considered variants as that term is used herein even if the structure of one of the molecules is not found in the other, or if the sequences of amino acid residues are not identical. The term 'analog' is meant to refer to a protein that differs structurally from the wild type AHS or AHS transcriptional regulator, but possesses similar activity.

A "biologically inactive derivative thereof" is a AHS or a AHS transcriptional regulator that is modified by amino acid deletion, addition, substitution, or truncation, or that has been chemically derivatized, that has reduced function or does not function in the same manner as the wild type protein of SEQ ID NO:15-28. For example, a frame-shift mutation would likely result in reduced function or elimination of function.

A recombinant or derived polypeptide is not necessarily translated from a designated nucleic acid sequence; it may be generated in any manner, including for example, chemical synthesis, or expression of a recombinant expression system. In addition the polypeptide can be fused to other proteins or polypeptides which increase its antigenicity, such as adjuvants for example.

As noted above, the methods of the present invention are suitable for production of any polypeptide of any length, via insertion of the above-described nucleic acid molecules or vectors into a host cell and expression of the nucleotide sequence encoding the polypeptide of interest by the host cell. Introduction of the nucleic acid molecules or vectors into a host cell to produce a transformed host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986). Transformations into yeast are typically carried out according to the method of Van Solingen et al., 1977, *J. Bact.*, 130, 946 and Hsiao et al. 1979, *Proc Natl Acad Sci USA* 76, 3829-3833. Once transformed host cells have been obtained, the cells may be cultivated under any physiologically compatible conditions of pH and temperature, in any suitable nutrient medium containing assimilable sources of carbon, nitrogen and essential minerals that support host cell growth. Recombinant polypeptide-producing cultivation conditions will vary according to the type of vector used to transform the host cells. For example, certain expression vectors comprise regulatory regions which require cell growth at certain temperatures, or addition of certain chemicals or inducing agents to the cell growth medium, to initiate the gene expression resulting in the production of the recombinant polypeptide. Thus, the term "recombinant polypeptide-producing conditions," as used herein, is not meant to be limited to any one set of cultivation conditions. Appropriate culture media and conditions for the above-described host cells and vectors are well-known in the art.

Following its production in the host cells, the polypeptide of interest may be isolated by several techniques. To liberate the polypeptide of interest from the host cells, the cells are lysed or ruptured. This lysis may be accomplished by contacting the cells with a hypotonic solution, by treatment with a cell wall-disrupting enzyme such as lysozyme, by sonication, by treatment with high pressure, or by a combination of the above methods. Other methods of cell disruption and lysis that are known to one of ordinary skill may also be used.

Following disruption, the polypeptide may be separated from the cellular debris by any technique suitable for separation of particles in complex mixtures. The polypeptide may then be purified by well known isolation techniques. Suitable techniques for purification include, but are not limited to, ammonium sulfate or ethanol precipitation, acid extraction, electrophoresis, immunoadsorption, anion or cation exchange chromatography, phosphocellulose chromatography, hydrophobic interaction chromatography, affinity chromatography, immunoaffinity chromatography, size exclusion chromatography, liquid chromatography (LC), high performance LC (HPLC), fast performance LC (FPLC), hydroxylapatite chromatography and lectin chromatography.

The recombinant or fusion protein can be used as a diagnostic tool and in a method for producing antibodies against AHS or AHS transcriptional regulator, detectably labeled and unlabeled, or as a bait protein in an assay to isolate proteins or target gene which interact with AHS or AHS transcriptional regulator. The transformed host cells can be used to analyze the effectiveness of drugs and agents which inhibit AHS or AHS transcriptional regulator function, such as host proteins or chemically derived agents or natural or synthetic drugs and other proteins which may interact with the cell to down-regulate or alter the expression of AHS or AHS transcriptional regulator, or its cofactors.

In another embodiment, the present invention relates to monoclonal or polyclonal antibodies specific for the above-described recombinant proteins (or polypeptides). For instance, an antibody can be raised against a peptide described above, or against a portion thereof of at least 10 amino acids, perferrably, 11-15 amino acids. Persons with ordinary skill in the art using standard methodology can raise monoclonal and polyclonal antibodies to the protein (or polypeptide) of the present invention, or a unique portion thereof. Material and methods for producing antibodies are well known in the art (see for example Goding, in, Monoclonal Antibodies: Principles and Practice, Chapter 4, 1986).

The level of expression of AHS or AHS transcriptional regulator, can be detected at several levels. Using standard methodology well known in the art, assays for the detection and quantitation of AHS or AHS transcriptional regulator RNA can be designed, and include northern hybridization assays, in situ hybridization assays, and PCR assays, among others. Please see e.g., Maniatis, Fitsch and Sambrook, Molecular Cloning; A Laboratory Manual (1982) or DNA Cloning, Volumes I and II (D. N. Glover ed. 1985), or Current Protocols in Molecular Biology, Ausubel, F. M. et al. (Eds), Wiley & Sons, Inc. for general description of methods for nucleic acid hybridization. Polynucleotide probes for the detection of AHS or AHS transcriptional regulator RNAs can be designed from the sequence. For example, RNA isolated from samples can be coated onto a surface such as a nitrocellulose membrane and prepared for northern hybridization. In the case of in situ hybridization of biopsy samples for example, the tissue sample can be prepared for hybridization by standard methods known in the art and hybridized with polynucleotide sequences which specifically recognize AHS or AHS transcriptional regulator RNA. The presence of a hybrid formed between the sample RNA and the polynucleotide can be detected by any method known in the art such as radiochemistry, or immunochemistry, to name a few.

One of skill in the art may find it desirable to prepare probes that are fairly long and/or encompass regions of the amino acid sequence which would have a high degree of redundancy in the corresponding nucleic acid sequences. In other cases, it may be desirable to use two sets of probes simultaneously, each to a different region of the gene. While the exact length of any probe employed is not critical, typical probe sequences are no greater than 500 nucleotides, even more typically they are no greater than 250 nucleotides; they may be no greater than 100 nucleotides, and also may be no greater than 75 nucleotides in length. Longer probe sequences may be necessary to encompass unique polynucleotide regions with differences sufficient to allow related target sequences to be distinguished. For this reason, probes are preferably from about 10 to about 100 nucleotides in length and more preferably from about 20 to about 50 nucleotides.

The DNA sequence of AHS or AHS transcriptional regulator can be used to design primers for use in the detection of AHS or AHS transcriptional regulator using the polymerase chain reaction (PCR) or reverse transciption PCR (RT-PCR) such as those listed in Table 2 below. The primers can specifically bind to the AHS or AHS transcriptional regulator cDNA produced by reverse transcription of AHS or AHS transcriptional regulator RNA, for the purpose of detecting the presence, absence, or quantifying the amount of AHS or AHS transcriptional regulator RNA by comparison to a standard. The primers can be any length ranging from 7-40 nucleotides, preferably 10-15 nucleotides, most preferably 18-25 nucleotides homologous or complementary to a region of the AHS or AHS transcriptional regulator sequence. Reagents and controls necessary for PCR or RT-PCR reactions are well known in the art. The amplified products can then be analyzed for the presence or absence of AHS or AHS transcriptional regulator sequences, for example by gel fractionation, by radiochemistry, and immunochemical techniques. This method is advantageous since it requires a small number of cells. Once AHS or AHS transcriptional regulator is detected, a determination whether the cell is overexpressing or underexpressing AHS or AHS transcriptional regulator can be made by comparison to the results obtained from a normal cell using the same method. Decreased AHS or AHS transcriptional regulator may be an indication of reduced virulence of the infecting bacteria, or an indication that tissue-specific or site-specific expression of the gene is reduced.

In another embodiment, the present invention relates to a diagnostic kit for the detection of AHS or AHS transcriptional regulator RNA in cells, said kit comprising a package unit having one or more containers of AHS or AHS transcriptional regulator oligonucleotide primers for detection of AHS or AHS transcriptional regulator by PCR or RT-PCR or AHS or AHS transcriptional regulator polynucleotides for the detection of AHS or AHS transcriptional regulator RNA in cells by in situ hybridization or northern analysis, and in some kits including containers of various reagents used for the method desired. The kit may also contain one or more of the following items: polymerization enzymes, buffers, instructions, controls, detection labels. Kits may include containers of reagents mixed together in suitable proportions for performing the methods in accordance with the invention. Reagent containers preferably contain reagents in unit quantities that obviate measuring steps when performing the subject methods.

In a further embodiment, the present invention provides a method for identifying and quantifying the level of AHS or AHS transcriptional regulator present in a particular sample. Any of a variety of methods which are capable of identifying (or quantifying) the level of AHS or AHS transcriptional regulator in a sample can be used for this purpose.

Diagnostic assays to detect AHS or AHS transcriptional regulator may comprise a biopsy or in situ assay of cells from an organ or tissue sections, as well as an aspirate of cells from normal or disease tissue. In addition, assays may be conducted upon cellular extracts from organs, tissues, cells, urine, or serum or blood or any other body fluid or extract. Similarly, the assay may be applied to environmental samples, such as soil, water, and air.

When assaying a sample, the assay will comprise, contacting the sample to be assayed with a AHS or AHS transcriptional regulator ligand or substrate, natural or synthetic, or an antibody, polyclonal or monoclonal, which recognizes AHS or AHS transcriptional regulator, or antiserum capable of detecting AHS or AHS transcripitonal regulator, and detecting the complex formed between AHS or AHS transcriptional regulator present in the sample and the AHS or AHS transcriptional regulator ligand, substrate, or antibody added.

AHS or AHS transcriptional regulator ligands or substrates include for example, a downstream component in the quorum sensing pathway, a substrate for AHS, or an AHS transcriptional regulator interacting protein or DNA binding site, in addition to natural and synthetic classes of ligands and their derivatives which can be derived from natural sources such as animal or plant extracts.

AHS or AHS transcriptional regulator ligands or antibodies, or fragments of ligand and antibodies capable of detecting AHS or AHS transcriptional regulator may be labeled using any of a variety of labels and methods of labeling for use in diagnosis and prognosis of disease associated with Burkholderia. Examples of types of labels which can be used in the present invention include, but are not limited to, enzyme labels, radioisotopic labels, non-radioactive isotopic labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^{3}H$, $^{111}In$, $^{125}$ I, $^{32}P$, $^{35}S$, $^{14}C$, $^{57}To$, $^{58}Co$, $^{59}Fe$, $^{75}Se$, $^{152}Eu$, $^{90}Y$, $^{67}Cu$, $^{21}Ci$, $^{211}At$, 212 Pb, $^{47}Sc$, $^{109}Pd$, $^{11}C$., $^{19}F$, $^{123}I$, etc.

Examples of suitable non-radioactive isotopic labels include $^{157}Gd$, $^{55}Mn$, $^{162}Dy$, $^{52}Tr$, $^{46}Fe$, etc.

Examples of suitable fluorescent labels include a $^{152}Eu$ label, a fluorescein label, an isothiocyanate label, a rhodamine label, a phycoerythrin label, a phycodyanin label, an allophycocyanin label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label, etc.

Those of ordinary skill in the art will know of other suitable labels which may be employed in accordance with the present invention. The binding of these labels to ligands and to antibodies or fragments thereof can be accomplished using standard techniques commonly known to those of ordinary skill in the art. Typical techniques are described by Kennedy, J. H., et al., 1976 (*Clin. Chim. Acta* 70, 1-31), and Schurs, A. H. W. M., et al. 1977 (*Clin. Chim Acta* 81, 1-40). Coupling techniques mentioned in the latter are the glutaraldehyde method, the periodate method, the dimaleimide method, and others, all of which are incorporated by reference herein.

The detection of the antibodies (or fragments of antibodies) of the present invention can be improved through the use of carriers. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to AHS or AHS response regulator. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding monoclonal antibody, or will be able to ascertain the same by use of routine experimentation.

The ligands or antibodies, or fragments of antibodies or ligands discussed above may be used to quantitatively or qualitatively detect the presence of Burkholderia. Such detection may be accomplished using any of a variety of immunoassays known to persons of ordinary skill in the art such as radioimmunoassays, immunometic assays, etc. Using standard methodology well known in the art, a diagnostic assay can be constucted by coating on a surface (i.e. a solid support) for example, a microtitration plate or a membrane (e.g. nitrocelluolose membrane), antibodies specific for either antigen, i.e., AHS or AHS transcriptional regulator, or a portion or either antigen, and contacting it with a sample from a person suspected of having a Burkholderia related disease. The presence of a resulting complex formed between the antigen in the sample and antibodies specific therefor can be detected by any of the known detection methods common in the art such as fluorescent antibody spectroscopy or colorimetry. A good description of a radioimmune assay may be found in Laboratory Techniques and Biochemistry in Molecular Biology. by Work, T. S., et al. North Holland Publishing Company, N.Y. (1978), incorporated by reference herein. Sandwich assays are described by Wide at pages 199-206 of Radioimmune Assay Method, edited by Kirkham and Hunter, E. & S. Livingstone, Edinburgh, 1970.

The diagnostic methods of this invention are predictive of patients suffering from meliodosis, or glanders disease, or Burkholderia related diseases.

The protein can be used to identify inhibitors of AHS activity or AHS transcriptional regulator. Using asssays known in the art for quantitation of AHS, natural and synthetic agents and drugs can be discovered which result in a reduction or elimination of AHS or synthase activity. Knowledge of the mechanism of action of the inhibitor is not necessary as long as a decrease in the activity of synthase is detected. Inhibitors may include agents or drugs which either bind or sequester synthase substrate(s) or cofactor(s), or inhibit the synthase itself, directly, for example by irreversible binding of the agent or drug to the synthase, or indirectly, for example by introducing an agent which binds the synthase substrate. Agents or drugs related to this invention may result in partial or complete inhibition of synthase activity. Inhibitors of synthase may be used in the treatment or amelioration of glanders disease or meliodosis, and diseases associated with Burkholderia infection.

Similarly, agents which reduce the function of AHS transcriptional regulator, natural and synthetic agents and drugs can be discovered which result in a reduction or elimination of response regulator activity. Knowledge of the mechanism of action of the inhibitor is not necessary as long as a decrease in the activity of response regulator is detected. Inhibitors may include agents or drugs which inhibit binding of the signal produced by the synthase to the synthase transcriptional regulator, agents which inhibit binding of the transcriptional regulator itself, directly or indirectly to its target gene, for example by irreversible binding of the agent or drug to the response regulator, by inhibiting multimerization of the enzyme, by blocking the target gene binding site. Agents or drugs related to this invention may result in partial or complete inhibition of trancriptional regulator activity. Inhibitors of AHS transcriptional regulator may be used in the treatment or amelioration of glanders disease or meliodosis, and diseases associated with Burkholderia infection.

Agents which decrease AHS or AHS transcriptional regulator RNA include, but are not limited to, one or more ribozymes capable of digesting AHS or AHS transcriptional regulator RNA, or antisense oligonucleotides capable of hybridizing to AHS or AHS transcriptional regulator RNA such that the translation of AHS or AHS transcriptional regulator RNA is inhibited or reduced resulting in a decrease in the level of AHS or AHS transcriptional regulator. These antisense oligonucleotides can be administered as DNA, as DNA entrapped in proteoliposomes containing viral envelope receptor proteins (Kanoda, Y. et al., 1989, Science 243, 375) or as part of a vector which can be expressed in the target cell such that the antisense DNA or RNA is made. Vectors which are expressed in particular cell types are known in the art. Alternatively, the DNA can be injected along with a carrier. A carrier can be a protein such as a cytokine, for example interleukin 2, or polylysine-glycoprotein carrier. Such carrier proteins and vectors and methods of using same are known in the art. In addition, the DNA could be coated onto tiny gold beads and said beads introduced into the skin with, for example, a gene gun (Ulmer, J. B. et al., 1993, *Science* 259, 1745).

Alternatively, antibodies, or compounds capable of reducing or inhibiting the synthase or the synthase transcriptional regulator, that is reducing or inhibiting either the expression, production or activity of these proteins, such as antagonists, can be provided as an isolated and substantially purified protein, or as part of an expression vector capable of being expressed in the target cell such that the synthase-reducing or inhibiting agent is produced. In addition, co-factors such as various ions, i.e. $Ca2^{+}$ or factors which affect the stability of the enzyme can be administered to modulate the expression and function of synthase. These formulations can be administered by standard routes. In general, the combinations may be administered by the topical, transdermal, intraperitoneal, oral, rectal, or parenteral (e.g. intravenous, subcutaneous, or intramuscular) route. In addition, synthase-inhibiting compounds may be incorporated into biodegradable polymers being implanted in the vicinity of where drug delivery is desired, for example, at the site of infection or implanted so that the synthase-inhibiting compound is slowly released systemically. The biodegradable polymers and their use are described, for example, in detail in Brem et al.(1991) *J. Neurosurg.* 74, 441-446. These compounds are intended to be provided to recipient subjects in an amount sufficient to effect the inhibition of synthase. Similarly, agents which are capable of negatively affecting the expression, production, stability or function of synthase, are intended to be provided to recipient subjects in an amount sufficient to effect the inhibition of synthase. An amount is said to be sufficient to "effect" the inhibition or induction of synthase if the dosage, route of administration, etc. of the agent are sufficient to influence such a response.

In providing a subject, specifically equine or human, with agents which modulate the expression or function of synthase to a recipient patient, the dosage of administered agent will vary depending upon such factors as the patient's age, weight, height, sex, general medical condition, previous medical history, etc. In general, it is desirable to provide the recipient with a dosage of agent which is in the range of from about 1 pg/kg to 10 mg/kg (body weight of patient), although a lower or higher dosage may be administered.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences [16th ed., Osol, A. ed., Mack Easton Pa. (1980)]. In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacrylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

The present invention also provides kits for use in the diagnostic or therapeutic methods described above. Kits according to this aspect of the invention may comprise one or more containers, such as vials, tubes, ampules, bottles and the like, which may comprise one or more of the compositions of the invention.

The kits of the invention may comprise one or more of the following components, one or more compounds or compositions of the invention, and one or more excipient, diluent, or adjuvant.

In another embodiment, the present invention describes Burkholderia strains, specifically *B. mallei* and *B. pseudomallei* strains, merodiploid strains and other mutants in various AHS and LuxR genes (Table 1). Any alteration of one or more of AHS or AHS transcriptional regulator gene which results in an avirulent, live attenuated strain is part of the present invention. The strain GB8::bpmI3 is avirulent, but still able to produce a capsule similar to wild type. All animals (40%) challenged with wild type *B. mallei* after aerosol exposure to GB8::bpmI3 survived and no recoverable mutants were isolated from spleen extracts. GB8::bpmI1 also showed a significant reduction in virulence however, exposures to GB8::bpmI1 prior to challenge resulted in 0% survival of the experimental group. Viable organisms were recovered from the spleens of animals exposed to GB8::bpmI1. Other mutant strains wherein more that one synthase is missing, or a combination of synthase genes and response regulator genes are altered are likely to produce a mutant strain with the desired virulence and ability to protect against challenge. Specifically, by deleting the bmaI1, bmaI3, and bmaR5, genes, a combinatorial effect in the reduction of virulence observed for a single mutant should be beneficial in a single strain. Preferably, the mutation introduced is designed to be non-revertable, i.e. will not revert to wild-type.

The mutant strains, e.g. GB8::bpmI1 strain, or non-revertant mutant strains of *B. mallei* or *B. pseudomallei*, may function as a gene or gene product delivery system since the strain has reduced virulence, can penetrate the tissue, resides in the tissue for a specified period of time, and is eventually cleared from the tissue by the host. For example, it is envisioned that an antigen of interest could be delivered to an organ, specifically the lungs, which is naturally invaded by the bacterial delivery agent in a patient where the antigen can provide benefit. The antigen can be introduced into the bacterial delivery agent in a second plasmid. Alternatively, a second plasmid could be used to provide a source of vaccine antigen for pathogens found in organs naturally invaded by Burkholderia such as a systemic invasion, spleen, or kidney, lung, central nervous system, eye, to name a few.

Such strains represents a safe delivery vehicle and are advantageous because they can carry one or more compounds and can be genetically engineered to carry one or more nucleic acid molecules capable of effecting gene therapy and/or of encoding one or more proteins and/or RNA molecules. The compound of interest can be carried by such a strain, e.g. GB8::bpmI1 within the bacteria cell, on the membrane surface, in the capsule, spanning the membrane, withing the periplasm, and combinations thereof. At least some of the compound of interest remains associated with the bacteria at least until the bacteria reaches its target, or site of action (e.g. the bloodstream, interstitial tissue, or a cell), at which point it is also possible that a compound carried by the bacteria may be released. As used herein, a compound capable of protecting an animal or plant from disease is a compound that when administered to an animal or plant can prevent a disease from occuring and/or cure or alleviate disease symptoms or cause. Examples of diseases from which to protect an animal or plant include, but are not limited to, infections, genetic defects and other metabolic disorders. Such classes of diseases can lead to abnormal cell growth (e.g., benign or malignant neoplasia, hyperplastic syndromes), degenerative processes, and/or immunological defects as well as to a number of other disorders.

In accordance with the present invention, compounds included in the above-described delivery vehicles can have a variety of functions. Delivery vehicles of the present invention preferably include compounds capable of stimulating an immune response, compounds capable of suppressing an immune respone, toxic compounds, compounds capable of inhibiting transcription of a gene, compounds capable of inhibiting translation of a gene, compounds capable of inhibiting the ability of an infectious agent to produce progeny, compounds capable of replacing a defective gene, compounds capable of replacing a defective protein (including nucleic acid molecules capable of encoding such proteins and mimetopes of such proteins) and/or biological response modifiers (e.g., cytokines, such as lymphokines and monokines, as well as other growth modulating factors), and mixtures thereof. Examples of such compounds include, but are not limited to, antibiotics, antibodies, antifungal compounds, antigens, antiparasite compounds, antisense compounds, antiviral compounds, chemotherapeutic agents, cytokines, growth modulating factors (including both growth stimulants and suppressants), herbicides, hormones, immunosuppressants, nucleic acid-based drugs (e.g., DNA- or RNA-based drugs), nucleic acid molecules comprising coding regions, nucleic acid molecules comprising regulatory sequences, nucleoside analogs, other oligonucleotides, peptide analogs, peptides, pesticides, prodrugs (e.g., compounds that are activated at the site of action), other proteins, ribozymes, steroids, toxins, and/or vitamins.

Cell types naturally targeted by Burkholderia include, but are not limited to, lung, spleen, and kidney, among others.

The present invention includes the delivery of a composition comprising the delivery vehicle of the present invention to an animal or to a cell in culture. Such compositions can be delivered to an animal either in vivo or ex vivo, or can be delivered to cells in vitro. Such administration can be systemic, mucosal, and/or proximal to the location of the targeted cell type. Examples of routes to administer bacteria in vivo include aural, bronchial, genital, inhalatory, nasal, ocular, oral, parenteral, rectal, topical, transdermal, and urethral routes.

Ex vivo delivery refers to a method that includes the steps of contacting a population of cells removed from an animal with a composition comprising the delivery vehicle of the present invention under conditions such that the bacteria is adsorbed by targeted cell types and returning the contacted cells to the animal. Such a delivery method is particularly useful in the treatment of cells involved in hematopoiesis and the immune response as well as in the treatment of tumors.

In vitro delivery refers to the delivery of the delivery vehicle of the present invention to a population of cells (which can also include tissues or organs) in culture.

Methods to prepare and administer compositions via these routes are well known to those skilled in the art. A preferred single dose of a bacteria vehicle of the present invention is from about $1\times10^5$ to about $5\times10^7$ bacterial cell equivalents per kilogram body weight of the organism being administered the composition.

The mutant strains described above can be used for vaccine. In particular, the vaccine strain of the invention having a non-revertant mutation in bmaI3 and/or bmaI1 for a *B. mallei* vaccine to protect against glanders disease, or bpmI3 or bpmI1 for *B. pseudomallei* vaccine to protect against meliodosis. The similarity of the *B. mallei* and the *B. pseudomallei* genomes and diseases indicates that one vaccine should work against both diseases. The vaccine strain can be used directly in vaccine formulations, or lyophilized, as desired, using lyophilization protocols well known to the artisan. Lyophilized compositions will typically be maintained at about 4° C. When ready for use the lyophilized composition is reconstituted in a stabilizing solution, e.g., saline or comprising $Mg^{++}$ and HEPES, with or without adjuvant, as further described below.

Thus the vaccine of the invention contains as an active ingredient an immunogenically effective amount of a non-revertant, avirulent, *B. mallei* or *B. pseudomallei* strain having a mutation in one or more AHS gene or a mutation in one or more transcriptional regulator gene as described herein. The vaccine strain may be introduced into a host, particularly humans or equine, with a physiologically acceptable carrier and/or adjuvant or with another mutant strain having a different mutation in the same or different AHS gene or AHS transcriptional regulator gene to increase the effectiveness and/or safety of the vaccine. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

Administration of the vaccine strain disclosed herein may be carried out by any suitable means, including both parenteral injection (such as intraperitoneal, subcutaneous, or intramuscular injection), by in ovo injection in birds, orally and by topical application of the bacteria (typically carried in the pharmaceutical formulation) to an airway surface. Topical application of the bacteria to an airway surface can be carried out by intranasal administration (e.g. by use of dropper, swab, or inhaler which deposits a pharmaceutical formulation intranasally), by inhalation administration, such as by creating respirable particles of a pharmaceutical formulation (including both solid particles and liquid particles) containing the bacteria as an aerosol suspension, and then causing the subject to inhale the respirable particles. Methods and apparatus for administering respirable particles of pharmaceutical formulations are well known, and any conventional technique can be employed. As a result of the vaccination the host becomes at least partially or completely immune to *B. mallei* infection, or resistant to developing moderate or severe *B. mallei* infection.

The vaccine composition containing the vaccine strain of the invention can be administered to a person susceptible to or otherwise at risk of Burkholderia infection to enhance the individual's own immune response capabilities. Such an amount is defined to be a "immunogenically effective dose". In this use, the precise amount again depends on the patient's state of health and weight, the mode of administration, the nature of the formulation, etc., but generally range from about $1\times10^5$ to about $5\times10^7$ bacteria cell equivalents per kilogram body weight of the organism being administered the composition. In any event, the vaccine formulations should provide a quantity of the vaccine strain of the invention sufficient to effetively protect the patient against serious or life-threatening Burkholderia infection.

In some instances it may be desirable to combine the Burkholderia vaccines of the invention with vaccines which induce protective responses to other agents.

Single or multiple administration of the vaccine compositions of the invention can be carried out. Multiple administration may be required to elicit sufficient levels of immunity. Levels of induced immunity can be monitored by measuring amount of neutralizing secretory and serum antibodies, and dosages adjusted or vaccinations repeated as necessary to maintain desired levels of protection. The vaccine may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

The following examples are included to demonstrate preferred embodiments of the invention. It should be appreciated by those of skill in the art that the techniques disclosed in the examples which follow represent techniques discovered by the inventors and thought to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The following MATERIALS AND METHODS were used in the examples that follow.

Bacterial Strains and Plasmids:

The bacterial strains and cloning vectors in this study are described in Table 1. *B. thailandensis, Chromobacterium violaceum* CV026, *Agrobacterium tumefaciens* (A136), *Escherichia coli* and *B. pseudomallei* were cultured in Luria-Bertani (LB) broth or on LB agar at 30° C. or 37° C. as required. *B. mallei* was cultured in LB broth or LB agar with the addition of 4% glycerol. For the screening of recombinant clones *E. coli* was grown on LB plates containing 100 ug/ml ampicillin or 25 ug/ml kanamycin, 1 mM isopropyl-b-D-thiogalactopyranoside (IPTG), and 50 ug/ml 5-bromo-4-chloro-3-indolyl-b-D-galactoside (X-Gal).

Cloning the *B. Pseudomallei* Quorum Sensing Genes.

Genomic DNA from B. *pseudomallei* NCTC 4845 was digested with ClaI and ligated into similarly digested pBluescript KS+. The plasmids were transformed into *E. coli* JM109 pSB401 by electroporation. Plasmid pSB401 contains all the genes from *Photobacterium fischeri* required for bioluminescence except luxI. Therefore, only inserts in pBluescript encoding a luxI homolog capable of producing AHLs was able to induce bioluminescence, and thus produce colonies emitting light.

AHL Reporter Assays.

DW503 quorum mutants were analyzed for AHL synthesis using bioreporter strains that respond to exogenously secreted AHLs or varying composition. Using a cross feeding assay, the reporter strain (CV026 or A136) was streaked vertically on a 100×15 mm LB Petri plate, while the mutant strain was inoculated horizontally. For analysis, incorporation A136, strains were streaked onto LB plates containing 50 ug/ml X-Gal and incubated for 24-48 hrs at 37° C. For CV026, plates were generally incubated for 24 hr at 30° C. (9+10). Pigment production by CV026 or bluing of A136 at the junction site indicates AHL synthesis and secretion.

Exoproduct Secretion and Motility Analysis.

Siderphore activity was measured on CAS agar plates using methods previously described. Briefly, DW503 mutants and wild type DW503 were tooth picked onto CAS plates and incubated for 24-48 hrs at 37° C. Iron removal, indicative of siderphore secretion, was assayed by measuring the blue-orange halo surrounding the inoculation site. Protease and lipase secretion was monitored using methods described by DeShazer et al. To assay for hemolysis and or rhamnolipid biosynthesis, colonies were tooth picked onto 5% sheep blood agar plates and incubated for 24-72 hrs at 37° C. Hemolysis was indicated by a clearing of the erythrocytes around the site of inoculation. Twitching and swarming motility was examined using methods described by Kohler et al. and Reimmann et al. Plates were incubated at 30° C. for 48-72 hrs.

AHL Extraction, TLC, and MS Analysis.

Extraction of AHLs from culture supernatants and preparative TLC was performed as described by Shaw et al. TLC scrapings tentatively identified as containing AHLs were extracted three times with 1 ml of methylene chloride (HPLC grade; B&J, VWR Scientific, Bridgeport, NJ). Stationary phase material was pelleted by centrifugation at 4,000 rpm for 10 min. Supernatants were pooled and evaporated to dryness at 50° C. under a gentle stream of nitrogen. Dried samples were reconstituted in 100 ul of 50% acetonitrite (HPLC grade) in 0.1% formic acid.

Aliquots (20 ul) were injected onto a PepMap C18 column (150×1 mm, 5 u, 100 A) (LC Packings, San Francisco, Calif.). An ABI 140B syringe pump (Applied Biosystems, Foster City, Calif.) provided a flow rate of 50 ul/min, which was used with a 20 min gradient of 0 to 100% B to elute the compounds of interest. Solvent A consisted of 0.1% formic acid, and solvent B contained 0.1% formic acid in 95% acetonitrile. The column effluent was directed into a Finnigan DECA ion trap mass spectrometer fitted with an API II electrospray interface. The transfer capillary temperature was 350° C. Full scan, positive ion spectra were acquired by scanning from m/z 100 to m/z 335 in 1.5 sec. For identification, components were fragmented by collision-induced dissociation of the respective [M+H]+ ion using a relative collision energy setting of 19. These spectra were acquired by scanning from m/z 50 to m/z 335 in 1.5 sec. MS/MS spectra of unknowns were compared to those of standard compounds acquired under the same instrumental conditions for confirmation of identity.

Primer Design

Primer design for each allele was based upon reference to the *B. pseudomallei* K96243 genome project. Genomic DNA for PCR amplification was purified using the MasterPure™ DNA purification kit according to the manufacturer's instructions (Epicentre Technologies, Madison, Wis.). Internal gene fragments were PCR amplified with the primer pairs listed in Table 2 using the following conditions: one cycle at 94° C. for 5 min, 30 cycles at 94° C. for 30 sec, 56° C. for 30 sec, 72° C. for 30 sec, followed by a final 7 min extension at 72° C. For confirming site-specific integration, the extension time was increased to 4 min. All PCR reactions were performed with the Epicentre FailSafe kit using buffer "J" (Epicentre Technologies). Reactions were analyzed on a 0.8% agarose gel containing ethidium bromide (43) and subcloned into pCR2.1-TOPO (Invitrogen, Carlsbad, Calif.). Ligations were transformed into One Shot® chemically competent *E. coli* (Invitrogen) and screened by standard methods (43).

Mutant Construction and Confirmation:

Disruption cassettes were made by digesting pCR2.1-TOPO containing internal gene amplicons for each of the eight quorum loci with EcoR1 (New England Biolabs, Beverly, Mass.) for 1 hr at 37° C. Digestions were heat inactivated and subcloned into the suicide vector pGSV3 (McClean et al., 1997, supra) using the Epicentre Fast-Link DNA ligation kit (Epicentre Technologies). Ligations were chemically transformed as described above and screened on LB plates containing 10 μg/ml of gentamycin (Sigma). Random colonies (five from each transformation) were inoculated into 2 ml of LB broth containing 10 μg/ml of gentamycin and incubated at 37° C. for 16-18 hr with agitation. Plasmid DNA was purified using the Wizard Plus Miniprep kit (Promega, Madison, Wis.), digested as described above, and analyzed on a 0.8% agarose gel with ethidium bromide. Clones containing inserts were electrically transformed into *E. coli* SM10 and mobilized into *B. thailandensis* DW503, (Simon et al., 1989, supra). Transconjugants were selected on LB plates containing 10 μg/ml of gentamycin and 15 μg/ml of polymyxin (Sigma). Genomic DNA from transconjugants, three mutants from each mating experiment, was purified using methods described above. Site-specific integration, indicated by a 3.0 Kb increase in amplicon size corresponding to the suicide vector, was confirmed using PCR methods previously described for target gene amplification incorporating an extension time of 4 min.

Whole body Aersol Exposures:

Approximately 48 hr prior to challenge 3 ml cultures were individually inoculated with wild-type *B. mallei* and each quorum mutant and incubated for 24 hr at 37° C. A 1 ml aliquot from the 3 ml overnight cultures was used to inoculate 25 ml of LBG. Cultures were incubated at 37° C. for 18 hr, optical densities ($OD_{660}$) measured, and 10 ml (approximately $10^9$ colony forming units/ml) was delivered to groups of 10 mice via nebulization using methods described by Jeddeloh et. al. (2002, supra). Chamber concentration was determined by CFU enumeration from air samples collected within the exposure compartment and the relative inhaled dose was deciphered by factoring the number of respirations for 6 week-old BALB/c mice (Jeddeloh et al., 2002, supra).

Organ Loads:

The relative bacterial loads within the spleen, liver, and lungs of female BALB/c mice challenged with each *B. mallei* and *B. pseudomallei* mutant and wild type strains was assayed over a 5 day period. Animals were humanly euthanized using $CO_2$, organs extracted, and homongized in 1 ml of sterile PBS. Organ extracts were serially diluted, plated onto LBG containing 10 μg/ml of gentamycin, and incubated for 48 hr at 37° C.

EXAMPLE 1

Using the cepIR and lasIR genes as digital probes, several AHSs and transcriptional regulators were identified within the K96243 genome. Given the genetic similarity between *B. thailandensis* DW503 and *B. pseudomallei* 1026b, only small internal gene amplicons corresponding to each quorum allele were PCR amplified (FIG. 1) and sequenced from each strain. Nucleotide comparisons between the *B. thailandensis* DW503 and *B. pseudomallei* 1026b quorum genes demonstrated significant DNA homology (data not shown). PCR amplification and BLASTX search results further confirmed that the *B. thailandensis* DW503 genome encodes three AHS and five putative transcriptional regulators belonging to the LuxIR family of quorum proteins.

EXAMPLE 2

Gene Alignments for *B. Pseudomallei.*

The identified *B. pseudomallei/mallei* quorum genes share similarity with AHS and AHL receptors from *Burkholderia vietnamiensis, Ralstonia solanaserum, Burkholderia multivorans*, and *P. aeroginosa.* All of the AHS genes identified encode AHL-synthases of the autoinduce 1 (AI 1) sub-family and therefore are conceivably involved with intraspecies communication. Neither the *B. mallei* nor *B. pseudomallei* genome contained a *V. fishcheri* lusX-like AI 2 subfamily synthase. Merodiploids in each of the eight genes identified were constructed and phenotypically characterized using multiple assays. Disruption of bpmI1 and bpmRI affected quorum signaling in the *Chromobactirium violaceum* reporter strain CV026. In contrast, disruption of the bpmI3, R3 and R5 ORFs induced a hyper-hemolytic phenotype and enhanced siderophore secretion in *B. thailandensis*. In addition, lipase secretion, swarming and twitching motility were also effected by quorum disruptions. Loss-of-function mutations that produce gain-of-function phenotypes indicate this quorum network operates using both positive and negative signaling.

TABLE 1

Bacterial strains and plasmids used in this study

| Strain or Plasmid | Description | Reference or Source |
|---|---|---|
| *Escherichia Coli* | | |
| SM10 | Mobilizing strain; RP4 tra genes; $Km^r$ | Simon et al, 1983 |
| TOP10 | Used for cloning and blue-white screening | Invitrogen |
| *Burkholderia Mallei* | | |
| ATCC 23344 | Human isolate | USAMRIID |
| *Burkholderia pseudomallei* | | |
| DD503 | Δ(amrR-oprA) rpsL ($Sm^r$) $AG^s$ $Tc^s$ | Moore et al., 1999 |
| BTRJ10 | DD503 derivative; I1::pGSV3; $Gm^r$ | This study |
| BTRJ12 | DD503 derivative; I2::pGSV3; $Gm^r$ | This study |
| BTRJ13 | DD503 derivative; I3::pGSV3; $Gm^r$ | This study |
| BTRJ14 | DD503 derivative; R1::pGSV3; $Gm^r$ | This study |
| BTRJ15 | DD503 derivative; R2::pGSV3; $Gm^r$ | This study |
| BTRJ16 | DD503 derivative; R3::pGSV3; $Gm^r$ | This study |
| BTRJ17 | DD503 derivative; R4::pGSV3; $Gm^r$ | This study |
| BTRJ18 | DD503 derivative; R5::pGSV3; $Gm^r$ | This study |
| BTRJ19 | ATCC 23344 derivative; I1::pGSV3; $Gm^r$ | This study |
| BTRJ20 | ATCC 23344 derivative; I3::pGSV3; $Gm^r$ | This study |
| BTRJ21 | ATCC 23344 derivative; R1::pGSV3; $Gm^r$ | This study |
| BTRJ22 | ATCC 23344 derivative; R3::pGSV3; $Gm^r$ | This study |
| BTRJ23 | ATCC 23344 derivative; R4::pGSV3; $Gm^r$ | This study |
| BTRJ24 | ATCC 23344 derivative; R5::pGSV3; $Gm^r$ | This study |

TABLE 1-continued

Bacterial strains and plasmids used in this study

| Strain or Plasmid | Description | Reference or Source |
|---|---|---|
| Plasmids | | |
| pGSV3 | Mobilizable suicide vector; $Gm^r$ | McClean et al. 1997 |
| pCR2.1-TOPO | TA cloning vector; $Km^r$ $Ap^r$ | Invitrogen |
| pBHR1 | Mobilizable broad-host-range vector; $Km^r$ Cm | MoBiTec |
| pRUI1 | Contains a 369 bp PCR product from the 1026b I1 synthase gene | This study |
| pRUI2 | Contains a 360 bp PCR product from the 1026b I2 synthase gene | This study |
| pRUI3 | Contains a 398 bp PCR product from the 1026b I3 synthase gene | This study |
| pRUR1 | Contains a 397 bp PCR product from the 1026b R1 transcriptional regulator | This study |
| pRUR2 | Contains a 424 bp PCR product from the 1026b R2 transcriptional regulator | This study |
| pRUR3 | Contains a 402 bp PCR product from the 1026b R3 transcriptional regulator | This study |
| pRUR4 | Contains a 391 bp PCR product from the 1026b R4 transcriptional regulator | This study |
| pRUR5 | Contains a 401 bp PCR product from the 1026b R5 transcriptional regulator | This study |

TABLE 2

Primers used for PCR amplification of internal gene amplicons

| Gene[a] | Primer sequence | | Amplicon size |
|---|---|---|---|
| bthI1 | F5'-CCGCGACGACGACGGGGAAATC-3', | SEQ ID NO: 29 | 369 bp |
| | R5'-TCGATCCAGCACGCGACGACCAT-3', | SEQ ID NO: 30 | |
| bthI2 | F5'-ATAAGCGCCGCGCAACTGGATTCC-3', | SEQ ID NO: 31 | 360 bp |
| | R5'-CAGGATCGCCGTATTGCGGTGAGC-3', | SEQ ID NO: 32 | |
| bthI3 | F5'-TCGCGGGCCGATTGAACGAACTGC-3', | SEQ ID NO: 33 | 398 bp |
| | R5'-GAGCGACGCGGCCACCGTGAGCAC-3', | SEQ ID NO: 34 | |
| bthR1 | F5'-CGGCTTCGAATATTGCTGCTATGG-3', | SEQ ID NO: 35 | 397 bp |
| | R5'-GAGAAAACGGCTCATCAGCGAGTG-3', | SEQ ID NO: 36 | |
| bthR2 | F5'-AGCGACCGGCCCGTGACCTGGAG-3', | SEQ ID NO: 37 | 424 bp |
| | R5'-CGGCCTGTATCTTGTTCGTGGAG-3', | SEQ ID NO: 38 | |
| bthR3 | F5'-AGACGTCGTCTCGCTGCACTATCC-3', | SEQ ID NO: 39 | 402 bp |
| | R5'-ACCCACGTGAGGCACATCTGTTCG-3', | SEQ ID NO: 40 | |
| bthR4 | F5'-GGCGTTCGACAGATGAAACACGAC-3', | SEQ ID NO: 41 | 391 bp |
| | R5'-GCTCATCTGGCACGACGACCTCTA-3', | SEQ ID NO: 42 | |

TABLE 2-continued

Primers used for PCR amplification of internal gene amplicons

| Gene[a] | Primer sequence | | Amplicon size |
|---|---|---|---|
| bthR5 | F5'-CGCGTGCCGTGGCCGCTGTCCA-3', | SEQ ID NO: 43 | 401 bp |
| | R5'-CCGCGCTCCGGGTCCGCCATCAG-3', | SEQ ID NO: 44 | |

[a]bthI1-I3 correspond to AHSs while bthR1-R5 represent transcriptional regulators.

The *B. pseudomallei* quorum loci are similar to those of *B. mallei*. The loci are structurally complex and are flanked by several characterized and unknown proteins. The bpmIR1 and bpmIR2 alleles are divergently transcribed while the bpmR4 and bpmR5 are in a gene cluster that contains no putative AHL synthase. Intergenic disruption of this type have been identified in several species of Gram negative bacteria (McClean et al., 1997, supra; Moore et al., 1999, supra). Numerous orf's adjacent the bpmIR genes were identified in this study that have not been shown to be quorum regulated. Lewenza et al. (1998, supra) reported a $Mg^{2+}$ transport protein located downstream from cepR. The bpmR1, most similiar to bviR, also contained a $Mg^{2+}$ transport protein located downstream. The bpmIR2 loci are separated by a 3 kb intergenic region that contains two GeneMark predicted proteins with no similarity to known enzymes and a putative ion transport protein. Conway and Greenberg (2002, supra) reported that *B. vietnamiensis* produces an antibiotic that is potentially regulated by quorum sensing. Interestingly, positioned down stream from the bpmI2 gene is an orf that contains homology to several proteins involved antibiotic synthesis. Also, located upstream from the bpmR3 is a putative long-chain fatty-acid-CoA ligase protein. Conway and Greenberg (2002, supra) also reported the presence of a fabF-like gene located downstream from bviR. Mutational analysis of this gene indicated that fabF was not involved in acyl-ACP generation for bviI and did not influence AHL synthesis in *B.* vietnamiensis. The remaining bpm genes are flanked by several orf's with little or no similiarity to known gene products. None of the quorum genes characterized in this study are structurally orientented in the tail-tail position as seen in *P. aeruginosa*. The bpmIR1 and bpmIR2 are all divergently transcribed and contain intergenic regions while the bpmR4 and bpmR5 are orphaned for a corresponding AHS. Both of these genes exhibited similarity to LuxR type proteins and disruptions in these alleles resulted in verifiable phenotypes.

EXAMPLE 2

*B. Thailandensis* Quorum Sensing Mutants.

To assay for hemolysis and/or rhamnolipid biosynthesis, colonies were tooth picked onto 5% sheep blood agar plates and incubated at 37 C for 24-72 hours. Hemolysis was indicated by a clearing of the erythrocytes around the site of inoculation. Analysis of *B. thailandensis* and the engineered quorum mutants revealed that mutations in bpm::R1, bpm::R2, and bpm::R4 produced zones of hemolysis equivalent to that of wild type DW503. In contrast, mutations in bpm::I1 exhibited slight hemolysis while bpm::I2, bpm::I3, bpm::R3, and bpm::R5 disruptions revealed hyperhemolytic phenotypes with extensive beta hemolysis.

Twitching and swarming motility were examined using methods described by Reimmann et al. Plates were incubated at 30 C for 48-72 hrs. Mutations in the bpm::I2, bpm::R1, and bpm::R3 loci appeared to induce a defective twitching phenotype. Wild type DW503 colonies display a saucoidal symmetrical morphology without visible pigmentation. Mutations in the bpm::I3, bpmIIR3 exhibited a wrinkling phenotype in which the cells proliferated from the center of the inoculation site and grew on the surface of the underlying colony. Interestingly, bpm::R3 produced a faint orange pigment and displayed extensive wrinkling without the glistening appearance of DW503. Like twitching motility, quorum sensing also played a regulatory role for swarming motility in *B. thailandensis*. On swarm plates, DW503 grew in a irregular and spreading fashion at 24 hrs and completely colonized the entire plate after 36 hrs.

All the *B. thailandensis* quorum mutants produced this glistening exopolysaccharide on swarm plates. Mutations in bpm::I2 and bpm::R5 exhibited a defective swarming motility phenotype indicated by the inability to colonize 0.5% agar plates. In contrast, disruption of the bpm::R1 locus resulted in an enhanced capability of plate colonization.

Siderphore activity was measured on CAS agar plates using methods previously described. Briefly, DW503 mutants and wild-type DW503 were tooth picked onto CAS plates and incubated for 24-48 hrs at 37 C. Iron removal, indicative of siderphore secretion, was assayed by measuring the blue-orange halo surrounding the inoculation site. Protease and lipase secretion was monitored using methods described by DeShazer et al. Using each of the *B. thailandensis* AHL synthase and transcriptional regulator mutants, plate assays for hemolysis and detection of protease, siderphore, lipase and phospholipase C (PLC) were analyzed. Both PLC (egg yold plates) and protease production (3% skim milk) were not altered by any of the *B. thailandensis* quorum mutants tested in this study. Unlike protease synthesis, lipase secretion is both positively and negatively regulated by the *B. thailandensis* quorum sensing network. Mutations in the bpm::I2 and bpm::R2 genes produced a reduction (26.8% and 39%) in lipase biosynthesis while mutations in bpm::I1 and bpm::R1 (46.3% and 80.4%), bpm::I3 and bpm::R3 (70.2% and 107%), bpm::R4 (58.5%), and bpm::R5 (46.3%) demonstrated elevated levels of lipase secretion in comparison to DW503. Siderphore production was slightly enhanced in bpm::I3 and moderately elevated in bpm::R3 mutants. Levels of siderphore secretion for bpm::R1, bpm::R2, bpm::R4, and bpm::R5 were equivalent to that of DW503.

EXAMPLE 3

Site-specific integration of the internal gene fragment with the target *B. mallei* gene was confirmed using PCR with whole gene primers. Following recovery and confirmation, the mutants were subjected to a series of in vitro tests to determine which AHL signaling molecules they synthesize. The results of this analysis suggest that the BmaI1 and BpmI1 direct the synthesis of $C_8$-HSL and the bmaI3 and bpmI3 genes encode proteins that produce $C_6$-HSL. In contrast, the *B. pseudomallei* BpmI2 allows for the biosynthesis of N-decanoyl homoserine lactone. A thin liquid chromatography (TLC) based reporter assay (McClean, K. H. et al., 1997, Microbiology 143, 3703-3711; Zhang, Z. and L. S. Pierson III, 2001, Appl. Environ. Microbiol. 67, 4305-4315) in conjunction with mass spectrometry was used to confirm these results.

The AHS merodiploids in *B. mallei* were evaluated in whole body aerosol models (Jeddeloh, J. et al., 2003, Infect. Immun. 71, 584-587).

Female BALB/c mice were sprayed with approximately 50 LD50 (10,000CFU) using methods developed by USAMRIID. Challenges were performed by the aerobiology division within USAMRIID in a BL3 containment suite. Mice were sacrificed at day 7 and spleens were extracted. After homogenizing, 100 ul of a 5 ml extract was plated onto LB containing 4% glycerol (LBG) with 10 ug/ml gentamycin. To enumerate wild type *B. mallei*, extracts were plated onto LBG and incubated for 24-36 hrs at 37 C.

Figure 3A:
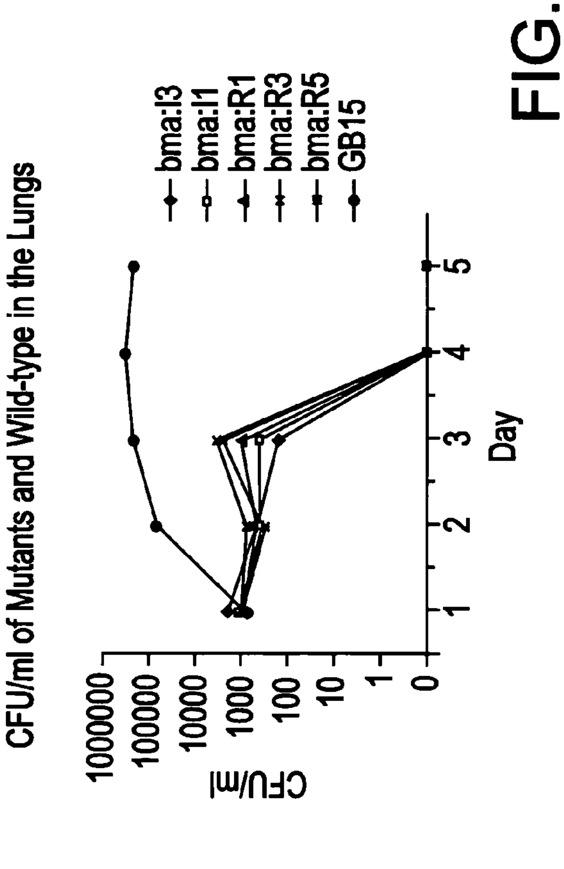
FIGS. 3A, 3B, 3C. The organ loads of female BALB/c mice aerosolized with *B. mallei* ATCC 23344 quorum sensing mutants. (A) represents the the number of viable organisms within the lungs, (B) depicts CFUs recovered from the spleen, and (C) demonstrates the organ loads in the liver. Animals were challenged with approximately $10^5$ CFUs of wild-type *B. mallei* ATCC 23344 and each quorum sensing mutant. Organs were extracted at days 1-5 and at day 30 post challenge. GB15 represents wild-type *B. mallei* ATCC 23344.
Figure 3B:
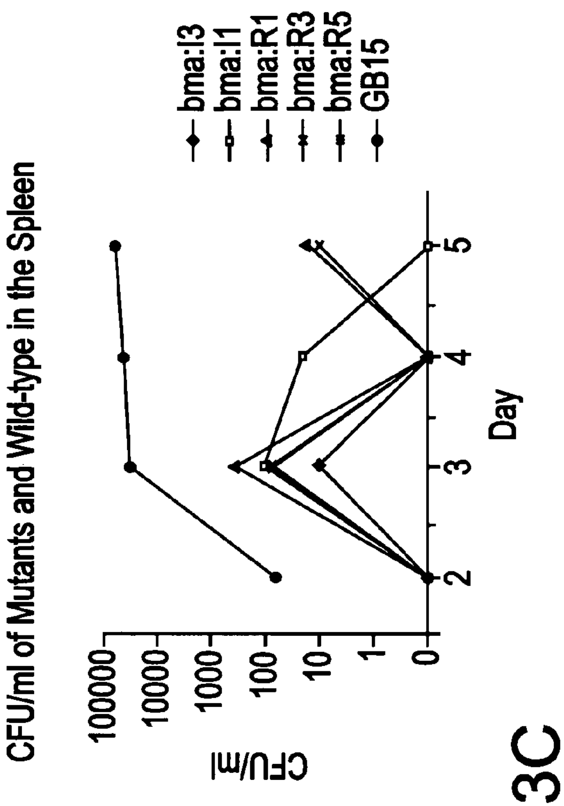
Figure 3C:
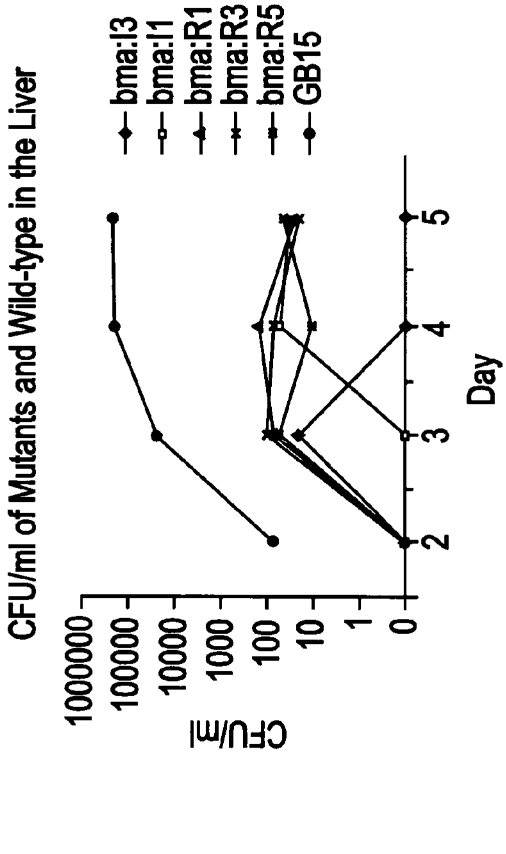

Both the GB8::bpmI1 and GB8::bpmI3 mutants were avirulent. Interestingly, the GB8::bpmI1 mutans were still able to colonize the spleen, liver and lungs of infected animals at days 1-5 post exposure (FIG. 3 and Table 3). At day 30, only the spleens contained recoverable GB8::bpmI1 mutants (FIG. 3). In contrast, the GB8::bpmI3 AHS mutants initially colonized the spleen and liver (FIG. 3) at days 1-5 but were cleared at day 30 (data not shown). Unlike the spleen and liver, the lungs of infected animals receiving GB8::bpmI1 and GB8::bpmI3 mutants were sterile by day 4 (FIG. 3) (The mixture of bmaI1 and bmaI3 mutants were not able to complement each other in trans.) Of the transcriptional regulator mutants, disruption of the bmaR3 and bmaR5 genes had the greatest effect on virulence. As with the *B. mallei* AHS mutants, the lungs of animals infected with LuxR mutants were cleared by day 4 (FIG. 3) post exposure. The spleen and liver of animals challenged with the *B. mallei* transcriptional mutants contained low bacterial loads in comparison to wild-type *B. mallei* (FIG. 3).

TABLE 3

Spleen loads from *B. mallei* aerosol challenges

| Organism Sprayed | Inhaled dose | Gmr spleen isolates | Gms spleen isolates | Total Recovered | Percent mutants | Percent wild-type |
|---|---|---|---|---|---|---|
| GB8::bpmI1 | 10906 | 3 | 17 | 19 | 10.5 | 89.5 |
| GB8::bpmI3 | 9800 | 0 | 0 | 0 | 0 | 0 |
| GB8::bpmR1 + WT GB8 | 10345 | 13 | 57 | 70 | 23 | 77 |
| GB8::bpmR3 + WT GB8 | 9975 | 17 | 54 | 71 | 31 | 69 |
| GB8::bpmR5 + WT GB8 | 11675 | 3 | 99 | 102 | 9 | 91 |
| GB8::DD3008 | 9468 | 0 | 41 | 41 | 0 | 100 |
| GB8::bpmI1 + GB8::bpmI3 | 8200 | 3 | 1 | 14 | 92.4 | 7.6 |

*a*A total of 10 mice were sprayed for each group and spleens were processed as described. GB8 is a Great Britain isolate and was used to create the merodiploids in this study. DD3008 is a *B. mallei* capsule mutant that fails to cause mortality in mice aerosol exposures. WT depicts wild type *B. mallei*.
*b*The inhaled dose was calculated by plating dilutions of nebulizer samples taken from each exposure pan containing 10 mice. The mathematical model for calculating the inhaled CFU's was developed by the aerobiology division at USAMRIID. Bacterial loads were numerated in triplicate by sacrificing 3 mice from each exposure group.

Figure 5:
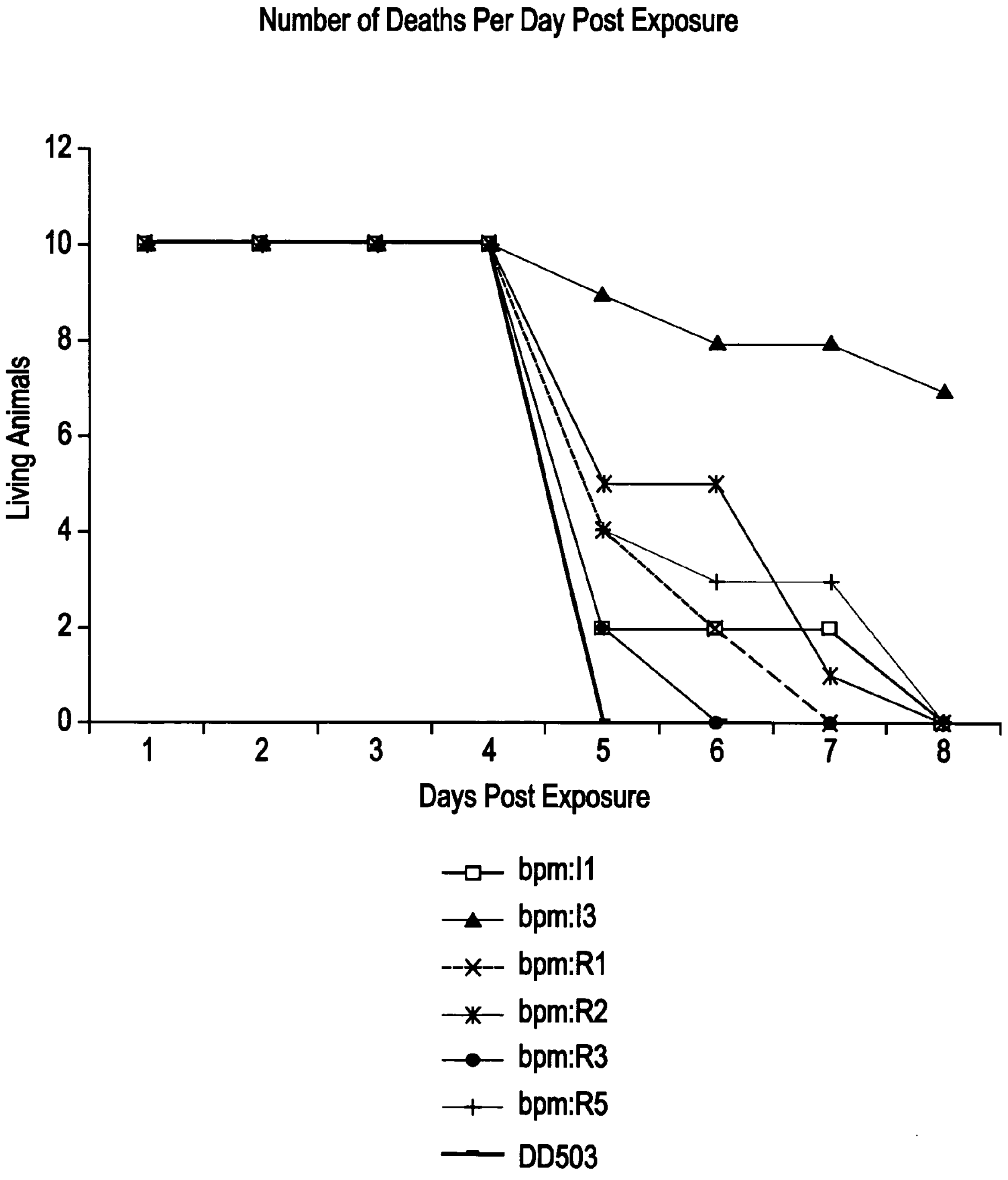
FIG. 5. Time to death of BALB/c mice infected with wild type *B. pseudomallei* DD503 and each quorum sensing mutants. Female BALB/c mice were aerosolized with approximately $10^5$ CFUs of wild type *B. pseudomallei* DD503 and each derivative quorum sensing mutant. Animal death was followed over a 29 day interval. DD503 represents wild type *B. pseudomallei.*

Unfortunately, the reduction in virulence observed in *B. mallei* was not as profound in *B. pseudomallei*. Of the eight *B. pseudomallei* quorum sensing mutants generated, only the DD503::bpmI3 displayed a reduction in pathogenicity using an aerosol BALB/c model (FIG. 5). Only 30% of the DD503::bpmI3 experimental group was lost over the 30 day experimental window in contrast to 100% for wild type DD503.

To date the only definitive virulence factor associated with the pathogenicity of *B. mallei* is extracellular capsule (DeShazer, D. et al., 2001, supra). All of the *B. mallei* quorum sensing mutants tested in this study produce capsule even those with reduced virulence. This is of significant importance indicating that this study has identified novel and previously unknown regulators of virulence and virulence gene expression.

Figure 4:
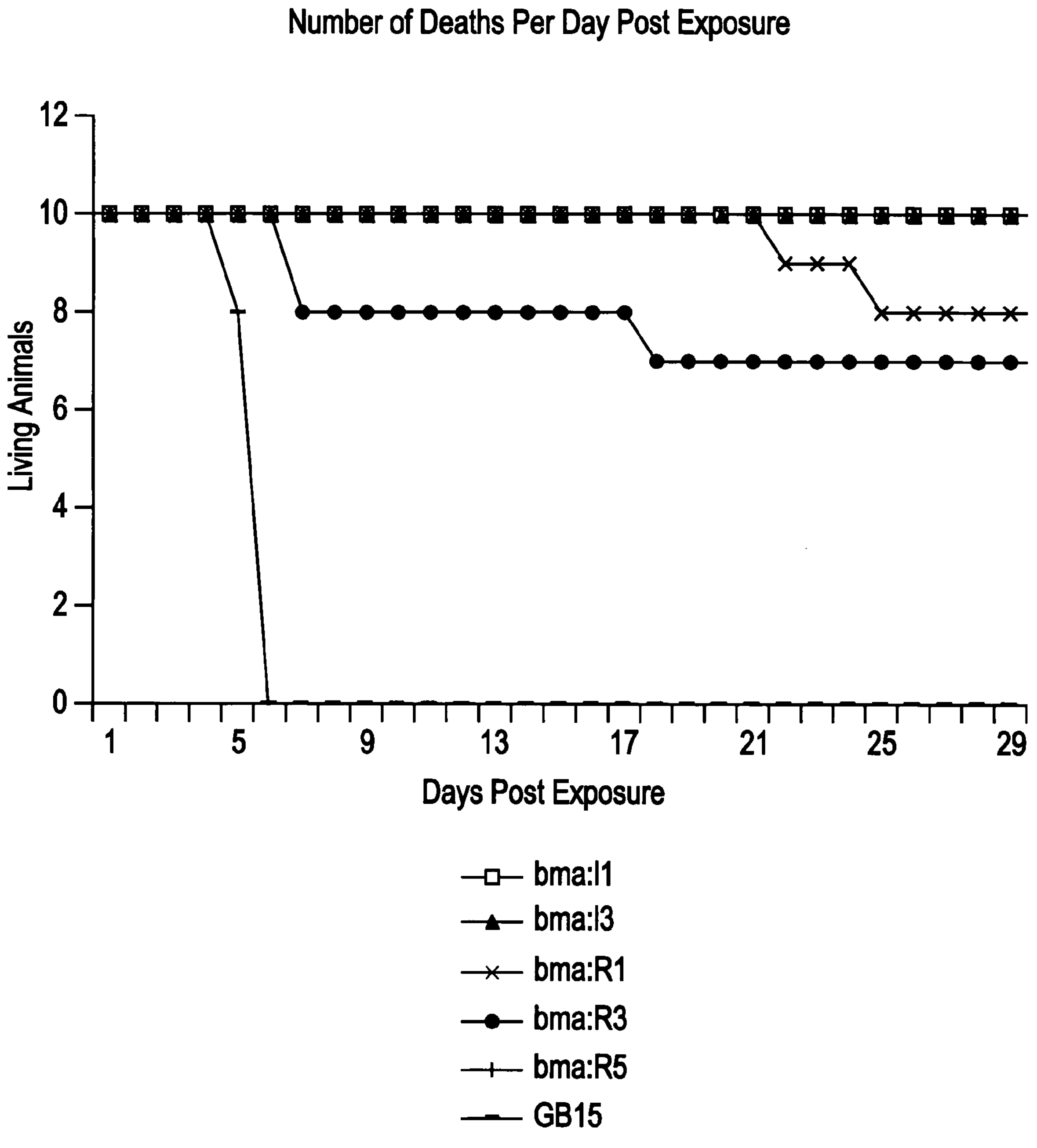
FIG. 4. Time to death of BALB/c mice infected with wild type *B. mallei* ATCC 23344 and each quorum sensing mutant. Female BALB/c mice were aerosolized with approximately $10^5$ CFUs of wild type *B. mallei* ATCC 23344 and each derivative quorum sensing mutant. Animal death was followed over a 29 day interval. GB15 represents wild type *B. mallei.*

Animals receiving the GB8::bpmI1 and GB8::bpmI3 mutants survived their initial aerosol challenge and were exposed again (FIG. 4) 21 days post exposure. Approximately 3 weeks following this secondary boost, animals were challenged with wild-type *B. mallei* ATCC 23344 (or GB8) by whole body aerosolization with 10 LD50s (around 10,000 CFU). The animals exposed to mutant derivatives received a similar dose for the initial and secondary challenges. Surprisingly, over a 21 day period, approximately 40% of the vaccinated animals exposed to GB8::bpmI3 survived while all memebers in the un-vaccinated group perished within 3 days. To our knowledge, the best performing whole-cell vaccine preparation only yields an extension in time to death by 1-2 days. Protection to 21 days has not been observed for a glanders vaccine previously.

What is claimed is:

1. A mutant *B. mallei* strain with reduced virulence wherein said strain is altered in expression or function of BmaI3 encoded by the sequence identified in SEQ ID NO:2.

2. An avirulent *B. mallei* strain devoid of BmaI3 activity wherein said BmaI3 is encoded by the sequence identified in SEQ ID NO:2.

3. A *B. mallei* vaccine strain comprising *B. mallei* having a nonrevertant mutation in bmaI3 specified in SEQ ID NO:2, wherein said strain has reduced virulence and is devoid of BmaI3 activity.

4. The *B. mallei* vaccine strain of claim 3 wherein said strain further contains another non-revertant loss-of-function mutation in a gene chosen from the group consisting of bmaI3, bmaI1, and bmaR5.

5. A vaccine comprising *B. mallei* vaccine strain according to claim 3 and a pharmaceutically acceptable carrier.

6. A vaccine comprising *B. mallei* vaccine strain according to claim 4 and a pharmaceutically acceptable carrier.

7. A method to elicit a *B. mallei* immune response in a mammal, said method comprising administering to said mammal a composition comprising the *B. mallei* vaccine strain of claim 3.

* * * * *